US008784824B2

(12) United States Patent
Zardi et al.

(10) Patent No.: US 8,784,824 B2
(45) Date of Patent: Jul. 22, 2014

(54) COMPOSITIONS AND METHODS FOR TREATMENT OF ANGIOGENESIS IN PATHOLOGICAL LESIONS

(75) Inventors: Luciano Zardi, Genoa (IT); Dario Neri, Zuricu (CH); Barbara Carnemolla, Genoa (IT); Fredrik Nilsson, Stockholm (SE); Lorenzo Tarli, Siena (IT); Laura Borsi, Genoa (IT); Cornelia Halin, Zurich (CH)

(73) Assignee: Philogen S.p.A., Siena (IT)

( * ) Notice: Subject to any disclaimer, the term of this patent is extended or adjusted under 35 U.S.C. 154(b) by 0 days.

(21) Appl. No.: 12/835,854

(22) Filed: Jul. 14, 2010

(65) Prior Publication Data
US 2010/0316602 A1 Dec. 16, 2010

Related U.S. Application Data

(62) Division of application No. 10/204,581, filed as application No. PCT/IB01/00382 on Feb. 22, 2001.

(60) Provisional application No. 60/184,767, filed on Feb. 24, 2000, provisional application No. 60/257,192, filed on Dec. 21, 2000.

(51) Int. Cl.
A61K 39/44 (2006.01)
C07K 16/00 (2006.01)

(52) U.S. Cl.
USPC .................. 424/178.1; 424/179.1; 530/391.1; 530/391.7

(58) Field of Classification Search
None
See application file for complete search history.

(56) References Cited

U.S. PATENT DOCUMENTS

| | | | |
|---|---|---|---|
| 5,650,150 | A | 7/1997 | Gillies |
| 5,660,827 | A | 8/1997 | Thorpe et al. |
| 5,776,427 | A | 7/1998 | Thorpe et al. |
| 5,855,866 | A | 1/1999 | Thorpe et al. |
| 5,863,538 | A | 1/1999 | Thorpe et al. |
| 5,965,132 | A | 10/1999 | Thorpe et al. |
| 7,273,924 | B1 | 9/2007 | Neri et al. |
| 7,622,556 | B2 | 11/2009 | Corti |
| 8,097,254 | B2 | 1/2012 | Neri et al. |

FOREIGN PATENT DOCUMENTS

| | | |
|---|---|---|
| EP | 0 344 134 A2 | 11/1989 |
| WO | WO 93-17715 | 9/1993 |
| WO | WO 96-01653 | 1/1996 |
| WO | WO 97-45544 | 12/1997 |
| WO | WO 99-58570 | 11/1999 |
| WO | WO 01-61017 | 8/2001 |
| WO | WO 01-62298 | 8/2001 |

OTHER PUBLICATIONS

Curnis et al., "Enhancement of tumor necrosis factor alpha antitumor immunotherapeutic properties by targeted delivery to aminopeptidase N (CD13)," Nat Biotechnol., (11):1185-90, 2000.*
Hoogenboom et al. Construction and expression of antibody-tumor necrosis factor fusion proteins. Mol Immunol. Sep. 1991;28(9):1027-37.*
Zetter BR., On target with tumor blood vessel markers. Nature Biotechnology, 15:1243-1244, 1997.*
Dellabona et al. Vascular attack and immunotherapy: a 'two hits' approach to improve biological treatment of cancer. Gene Therapy (1999) 6, 153-154.*
Mariani et al. A pilot pharmacokinetic and immunoscintigraphic study with the technetium-99m-labeled monoclonal antibody BC-1 directed against oncofetal fibronectin in patients with brain tumors. Cancer 80: 2484-2489.*
Gasparri et al. Tumor Pretargeting with Avidin Improves the Therapeutic Index of Biotinylated Tumor Necrosis Factor a in Mouse Models. Cancer Research 59, 2917-2923, Jun. 15, 1999.*
Rudikoff, S., et al., "Single Amino Acid Substitution Altering Antigen-Binding Specificity," Proc. Natl. Acad. Sci. USA, vol. 79, pp. 1979-1983, Mar. 1982.
Wagner, K., et al., "The Targeted Immunocytokine L19-IL2 Efficiently Inhibits the Growth of Orthotopic Panceatic Cancer," Cancer Therapy: Preclinical, Clin. Cancer Res 2008: 14(15), pp. 4951-4960, Aug. 1, 2008.
Johannsen, M., et al., "Phase I/II Study of the Tumor-Targeting Human L199-IL2 Monoclonal Antibody-Cytokine Fusion Protein in Patients with Advanced Renal Cell Carcinoma," Journal of Clinical Oncology, 2008 ASCO Annual Meeting Proceedings (Post-Meeting Edition), vol. 26, No. 15S (May 20 Supplement), 2 pages, 2008:16032.
Melkko, S., et al., "An Antibody-Calmodulin Fusion Protein Reveals a Functional Dependence Between Macromolecular Isoelectric Point and Tumor Targeting Performance," Int. J. Radiation Oncology Biol. Phys., vol. 54, No. 5, pp. 1485-1490, 2002.
Ebbinghaus, C., et al., "Engineered Vascular-Targeting Antibody-Interferon-γ Fusion Protein for Cancer Therapy," Int. J. Cancer:116, pp. 304-313 (2005).
Halin, C., et al., "Enhancement of the Antitumor Activity of Interleukin-12 by Targeted Delivery to Neovasculature," Nature Biotechnology, vol. 20, pp. 264-269, Mar. 2002.
Gafner, V., et al., "An Engineered Antibody-Interleukin-12 Fusion Protein with Enhanced Tumor Vacsular Targeting Properties," Int. J. Cancer: 119, pp. 2205-2212 (2006).

(Continued)

Primary Examiner — Maher Haddad
(74) Attorney, Agent, or Firm — Millen, White, Zelano & Branigan, PC

(57) ABSTRACT

Treatment of lesions of pathological angiogenesis, especially tumors, rheumatoid arthritis, diabetic retinopathy, age-related muscular degeneration, and angiomas. A conjugate is used comprising a molecule that exerts a biocidal or cytotoxic effect on target cells in the lesions and an antibody directed against an extracellular matrix component which is present in such lesions. The antibody may be directed against fibronectin-2 (IL-2), doxorubicin, interleukin-12 (IL-12), Interferon-γ (IFN-γ), Tumor Necrosis Factor α (TNFα) or Tissue Factor protein (which may be truncated).

24 Claims, 21 Drawing Sheets

(56) References Cited

OTHER PUBLICATIONS

Halin, C., et al., "Synergistic Therapeutic Effects of a Tumor Targeting Antibody Fragment, Fused to Interleuken 12 and to Tumor Necrosis Factor a[1]", Cancer Research, 63, pp. 3202-3210, Jun. 15, 2003.
Niesner, U., et al., "Quantitation of the Tumor-Targeting Properties of Antibody Fragments Conjugated to Cell-Permeating HIV-1 TAT Peptides," Bioconjugate Chem., 13, pp. 729-736, 2002.
Tarli, L., et al., Blood [Jul. 1999] 94(1): 192-198.
Lode, H.N., et al., "Natural Killer Cell-Mediated Eradication of Neuroblastoma Metastases to Bone Marrow by Targeted Interleukin-2 Therapy," Blood, vol. 91: pps. 1706-1715 (1998).
Lode, H.N., et al., "Targeted Interleukin-2 Therapy for Spontaneous Neuroblastoma Metastases to Bone Marrow," Journal of the National Cancer Institute, vol. 98, pp. 1586-1594 (1997).
Melani, C., et al., "Targeting of Interleukin 2 to Human Ovarian Carcinoma by Fusion with a Single-Chain Fv of Antifolate Receptor Antibody," Cancer Research, vol. 58, pp. 4146-4154 (1998).
Lode, H.N., et al., "Tumor-targeted IL-2 amplifies T cell-mediated immune response induced by gene therapy with single-chain IL-12," Proc. Natl. Acad. Sci., USA, vol. 96, pp. 8591-8596 (1999).
Epstein, A.L., et al., "Identification of a Monoclonal Antibody, TV-1, Directed against the Basement Membrane of Tumor Vessls, and its Use to Enhance the Delivery of Macromolecules to Tumors after Conjugation with Interleukin 2," Cancer Research, vol. 55: pp. 2673-2680 (1995).
Viti, F., et al., "Increased Binding Affinity and Valence of Recombinant Antibody Fragments Lead to Improved Targeting of Tumoral Angiogenesis," Cancer Research, vol. 59: pp. 347-352 (1999).
Neri, D., et al., "Affinity reagents against tumor-associated extracellular molecules and newforming vessels," Advanced Drug Delivery Reviews, vol. 31: pp. 43-52 (1998).
Neri, D., et al., "Targeting by affinity-matured recombinant antibody fragments of an angiogenesis associated fibronectin isoform," Nature Biotechnology, vol. 15: pp. 1271-1275, (1997).
Carnemolla, B., et al., "Phage Antibodies with Pan-Species Recognition of the Oncofetal Angiogenesis Marker Fibronectin ED-B Domain," Int. J. Cancer, vol. 68: 397-405 (1996).
Pini. A., et al., "Design and Use of a Phage Display Library," The Journal of Biological Chemistry, vol. 273, pp. 21769-21776 (1998).
Savage, et al., "A recombinant single chain antibody interleukin-2 fusion protein," Br. J. Cancer. Feb. 1993: 67(2): 304-310.
Becker, et al., "Eradication of human hepatic and pulmonary melanoma metastases in SCID mice by antibody-interleukin 2 fusion proteins," Proc. Natl. Acad. Sci., USA, Apr. 2, 1996; 93(7): 2702-2707.
Huang, et al., Tumor infarction in mice by antibody-directed targeting of tissue factor to tumor vasculature, Science, Jan. 24, 1997; 275(5299): 547-550.
Proleukin Efficacy in Metastatic Melanoma, Proleuikin Website, printed Aug. 2010, 2 pages.
Halin, C. et al., "Tumor-Targeting properties of Antibody-Vascular Endothelial Growth Factor Fusion Proteins," Int. J. Cancer, 2002, vol. 102, pp. 109-116.
Fell, H. P. et al., "Genetic Construction and Characterization of a Fusion Protein Consisting of a Chimeric F(ab') with Specificity for Carcinoma's and Human IL-2," The Journal of Immunology, Apr. 1, 1991, vol. 146, No. 7, pp. 2446-2452.
Allowed Claims of U.S. Appl. No. 11/783,274; Aug. 9, 2010.
BerndOrff, D., et al., "Radioimmunotherapy of Solid Tumors by Targeting Extra Domain B Fibronectin: Identification of the Best-Suited Radioimmunoconjugate," Clin. Cancer Res. 2005;11 (19 Suppl), Oct. 1, 2005, 7053s-7063s.
El-Emir, E., et al., "Characterisation and Radioimmunotherapy of L19-SIP, an Anti-Angiogenic Antibody Against the Extra Domain B of Fibronectin, in Colorectal Tumour Models," Brit. Jrnl. of Can. (2007) 96, 1862-1870.
Sauer, S., et al., "Expression of the Oncofetal ED-B Containing Fibronectin Isoform in Hematologic Tumors Enables ED-B Targeted 131I-L19SIP Radioimmunotherapy in Hodgkin Lymphoma Patients," Blood, 2009, 113: 2265-2274.
Tijink, B.M., et al., "Radioimmunotherapy of Head and Neck Cancer Xenografts Using $^{131}$I-Labeled Antibody L19-SIP for Selective Targeting of Tumor Vasculature," J. Nucl. Med. 2006; 47:1127-1135.
Tijink, B.M., et al., "$^{124}$I-L19-SIP for Immuno-PET Imaging of Tumour Vasculature and Guidance of $^{131}$I;L19-SIP Radioimmunotherapy," Eur. J. Nucl. Med. Mol. Imaging, DOI 10/1007/s00259-009-1096-y, Published online Mar. 4, 2009. 10 pages.
Borsi, L., et al., "Selective Targeting of Tumoral Vasculature: Comparaison of Different Formats of an Antibody (L19) to the ED-B Domain of Fibronectin," Int. J. Cancer: 102, 75-85 (2002).
Wyss, M.T., "Uptake of 18F-Flurocholine, $^{18}$F-FET, and $^{18}$F-FDG in C6 Gliomas and Correlation with $^{131}$I-SIP(L19), a Marker of Angiogenesis," The Jrnl of Nucl. Med., vol. 48, No. 4, Apr. 2007.
Gafner, V., et al., "An Engineered Antibody-Interleukin-12 Fusion Protein with Enhanced Tumor Vascular Targeting Properties," Int. J. Cancer: 119, 2205-2212 (2006).
Rondini, C.H., et al., "Enhancement of the Antitumor Activity of Interleukin-12 by Targeted Delivery to Neovasculature," Nature Biotechnology, vol. 20, Mar. 2002, 264-269.
Borsi, L., et al., "Selective Targeted Delivery of TNFα to Tumor Blood Vessels," Blood, Dec. 15, 2003, vol. 102, No. 13, 4384-4392.
Balza, E., et al., "Targeted Delivery of Tumor Necrosis Factor-α to Tumor Vessels Induces a Therapeutic T Cell-Mediated Immune Response that Protects the Host Against Syngeneic Tumors of Different Histologic Origin," Clin. Cancer Res., 2006; 12(8) Apr. 15, 2006, 2575-2582.
Carnemolla, B., et al., "Enhancement of the Antitumor Properties of Interleukin-2 by Its Targered Delivery to the Tumor Blood Vessel Extracellular Matrix," Blood, Mar. 1, 2002, vol. 99, No. 5, 1659-1665.
Schliemann, C., et al., "Complete Eradication of Human B-cell Lymphoma Xenografts Using Rituximab in Combination with the Immunocytokine L-19-IL2," Blood, 2009, 113: 2275-2283.
Menrad, A., et al., "ED-B Fibronectin as a Target for Antibody-Based Cancer Treatments," Expert Opin. Ther. Targets (2005) 9(3), 491-500.
DeMartis, S., et al., "Selective Targeting of Tumour Neovasculature by a Radiohalogenated Human Antibody Fragment Specific for the ED-B Domain of Fibronectin," Eur., J. Nucl. Med. vol. 28, No. 4, Apr. 2001, 534-539.
Spaeth, N., et al., "Radioimmunotherapy Targeting the Extra Domain B of Fibronectin in C6 Rat Gliomas: A Preliminary Study About the Therapeutic Efficacy of Iodine-131-Labeled SIP(L19)," Nuclear Medicine & Biology, 33 (2006) 661-666.
Xiang, R. et al., "Elimination of Established Murine Colon Carcinoma Metastases by Anti-body-Interleukin 2 Fusion Protein Therapy," Cancer Research, Nov. 1, 1997,vol. 57, pp. 4948-4955.
Becker, J. C. et al., "T Cell-mediated Eradication of Murine Metastatic Melanoma Induced by Targeted Interleukin 2 Therapy," J. Exp. Med., May 1996, vol. 183, pp. 2361-2366.
Tabata, M. et al., "Anti-angiogenic Radioimmunotherapy of Human Solid Tumors in Scid Mice Using $^{125}$I-Labeled Anti-Endoglin Monoclonal Antibodies," Int. J. Cancer, 1999, vol. 82, pp. 737-742.
Gillies, S. D. et al., "Antibody-IL-12 Fusion Proteins Are Effective in SCID Mouse Models of Prostate and Colon Carcinoma Metastases," The American Association of Immunologists, 1998, vol. 160, pp. 6195-6203.
Scherf, U. et al., "Cytotoxic and Antitumor Activitity of a Recombinant Tumor Necrosis Factor-B1(FV) Fusion Protein on LeY Antigen-expressing Human Cancer Cells," Clinical Cancer Research, Sep. 1996, vol. 2, pp. 1523-1531.
Qi, Y. et al., "Mouse Myeloma Cell Line Secreting Bifunctional Fusion Protein RM4/IFN-t Elicits Antitumor CD8 MHC Class I-Restricted T Cells That Are Cytolytic In Vitro and Tumoricidal In Vitro," Journal of Interferon and Cytokine Research, 1996, vol. 16, pp. 771-776.
Yang, H. M. et al., "Doxorubicin conjugated with a monoclonal antibody directed to a human melanoma-associated proteoglycan suppresses the growth of established tumor xenografts in nude mice," Proc. Natl. Acad. Sci., Feb. 1998, vol. 85, pp. 1189-1193.

(56) References Cited

OTHER PUBLICATIONS

Portolano et al., The Journal of Immunology, 1993, vol. 150, pp. 880-887.
Hemmerle, T., et al., "Tumor targeting properties of antibody fusion proteins based on different members of the murine tumor necrosis superfamily," Journal of Biotechnology, vol. 172 (2014), pp. 73-76.
Carnemolla, B., et al., "The Inclusion of the Type II Repeat ED-B in the Fibronectin Molecule Generates Conformational Modifications That Unmask a Cryptic Sequence," Journal of Biological Chemistry, vol. 267, No. 34, Dec. 5, pp. 24689-24692, 1992.
Khawli, L.A., Ph.D., et al., "Effect of Seven New Vasoactive Immunoconjugates on the Enhancement of Monoclonal Antibody Uptake in Tumors," Cancer Supplement, Feb. 1, 1994, vol. 73, No. 3, pp. 824-831.
Papadia, F.,Md., et al., "Isolated Limb Perfusion With the Tumor-Targeting Human Monoclonal Antibody-Cytokine Fusion Protein L19-TNF Plus Melphalan and Mild Hyperthermia in Patients with Locally Advanced Extremity Melanoma," Journal of Surgical Oncology, Published online in Wiley Online Library (wileyonlinelibrary.com), © 2012 Wiley Periodicals, Inc.—7 pages.
Spitaleri, G., et al., "Phase I/II study of the tumour-targeting human monoclonal antibody-cytokine fusion protein L19-TNF in patients with advanced solid tumours," J. Cancer Res. Clin. Oncol. (2013) 139: 447-455.
Weinstein, J.N., et al., "Local and Cellular Factors in the Pharmacology of Monoclonal Antibodies," Membrane-Mediated Cytotoxicity, pp. 279-289 © 1987 Alan R. Liss, Inc.
Response submitted to USPTO on Dec. 2, 2003 in U.S. Appl. No. 09/194,356, filed Sep. 2, 1999 (2 pages), along with a Declaration under 37 C.F.R. § 1.132 by Luciano Zardi, dated Nov. 18, 2003 (9 pages).
Response submitted to USPTO on Jan. 29, 2013 in U.S. Appl. No. 10/204,581, filed Mar. 10, 2003 (8 pages), along with a Declaration under 37 C.F.R. § 1.132 by Dr. Giovanni Neri, dated Nov. 13, 2012 (4 pages).
Office Action issued on Jun. 6, 2013 in co-pending U.S. Appl. No. 12/835,854, filed Jul. 14, 2010, 18 pages
Williams, J.A., et al., "Targeting and Therapy of Human Glioma Xenografts in Vivo Utilizing Radiolabeled Antibodies," Cancer Research, 1990: 50: 974s-979s.

Welt, S., et al., "Phase I/II Study of Iodine 125-Labeled Monoclonal Antibody A33 in Patients With Advanced Colon Cancer," Journal of Clinical Oncology, vol. 14, No. 6 Jun. 1996: pp. 1787-1797.
Oh, P., et al., "Subtractive proteomic mapping of the endothelial surface in lung and solid tumours for tissue-specific therapy," Nature, vol. 429, Jun. 10, 2004, pp. 629-635.
Tomlinson, et al., "The Repertoire of Human Germline $V_H$ sequences Reveals about Fifty Groups of $V_H$ Segments with Different Hypervariable Loops," 1992, J. Mol. Biol., vol. 227, pp. 776-798. [Exhibit 4 of Pini Declaration].
Cox et al., "A directory of human germ-line $V_x$ segments reveals a strong bias in their usage," 1994, Eur. J. Immunol., vol. 24, pp. 827-836. [Exhibit 5 of Pini Declaration].
Mao et al., Phage-display library selection of high-affinity human single-chain antibodies to tumour-associated carbohydrate antigens sialyl Lewis$^x$ and Lewis$^x$, 1999, Proc. Natl. Acad. Sci. USA, vol. 96, pp. 6953-6958. [Exhibit 6 of Pini Declaration].
Giovannoni et al., "Isolation of anti-angiogenesis antibodies from a large combinatorial repertoire by colony filter screening," 2001, Nucleic Acid Research, vol. 29, No. 5, e27. [Exhibit 7 of Pini Declaration].
Borsi, et al., "Preparation of Phage Antibodies to the ED-A Domain of Human Fibronectin," (1998), Experimental Cell Research, vol. 240, pp. 244-251.
Villa, et al., "A high-affinity human monoclonal antibody specific to the alternatively spliced EDA domain of fibronectin efficiently targets tumor neo-vasculature in vivo," (2008), Int. J. Cancer: 122, 2405-2413.
Rudnick, S.I., et al., "Affinity and Avidity in Antibody-Based Tumor Targeting," Cancer Biotherapy and Radiopharmaceuticals, vol. 24, No. 2, 2009, pp. 155-161.
Fujimori, K., et al., Modeling Analysis of the Global and Microscopic Distribution of Immunoglobulin G, F(ab')$_2$ and Fab in Tumors, Cancer Research, 49, Oct. 15, 1989, pp. 5656-5663.
Rosenberg, S.A., et al., Durability of complete responses in patients with metastatic cancer treated with high-dose interleukin-2: identification of the antigens mediating response. Ann Surg. 228: 307-317, 1998.
Matsuura, H., et al., "The oncofetal domain of fibronectin defined by monoclonal antibody FDC-6: its presence in fibronectins from fetal and tumor tissues and its absence in those from normal adult tissues and plasma," Proc. Nat'l Acad. Sci., USA, 82: 6517-6521, 1985.

* cited by examiner

| 8 days (mm³) | | 10 days (mm³) | | 13 days (mm³) | | 14 days (mm³) | |
|---|---|---|---|---|---|---|---|
| + | | + | | + | | + | |
| 78.000 | 148.000 | 75.000 | 267.00 | 268.000 | 460.00 | 397.000 | 816.00 |
| 41.000 | 39.000 | 140.000 | 47.000 | 201.000 | 774.000 | 349.000 | 1076.000 |
| 44.000 | 43.000 | 70.000 | 116.000 | 203.000 | 429.000 | 374.000 | 650.000 |
| 53.000 | 98.000 | 130.000 | 247.000 | 351.000 | 973.000 | 464.000 | 1046.000 |
| 54.000 | 62.000 | 102.000 | 110.000 | 588.000 | 528.000 | 596.000 | 708.000 |
| 76.000 | | 144.000 | | 445.000 | | 571.000 | |
| mean 57.6 | mean 78.0 | mean 110.2 | mean 157.4 | mean 342.7 | mean 632.8 | mean 458.5 | mean 859.2 |
| SD 15.80 | SD 45.56 | SD 32.69 | SD 137.50 | SD 152.24 | SD 233.48 | SD 104.41 | SD 516.92 |
| SE 6.45 | SE 20.37 | SE 13.35 | SE 42.53 | SE 62.15 | SE 104.42 | SE 42.62 | SE 86.75 |

SEQUENCE LISTING

```
<160> NUMBER OF SEQ ID NOS: 35

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 1

Ser Ser Ser Ser Gly Ser Ser Ser Gly Ser Ser Ser Ser Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Gly Gly Gly Gly Ser Gly Gly Gly Ser Gly Gly Gly Gly Ser
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 3

Gly Ser Ala Asp Gly Gly
1               5

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcgaattct cttcctcatc gggtagtagc tcttccggct catcgtccag cggcgcacct      60
acttcaagtt ctaca                                                      75

<210> SEQ ID NO 5
```

-continued

```
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcggatcct tatcaattca gatcctcttc tgagatgagt ttttgttcag tcagtgttga      60
gatgatgct                                                              69

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcgaattct ttgatttcca ccttggtccc                                       30

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgagtcattc gcggccgcag gtggcggtgg ctctggcact acaaatactg tggca            55

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 8

Gly Gly Gly Gly Ser
1               5

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtccttgtag tcaggccttt cacggaactc acctttctcc tggcccatac a                51

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agagaattct tattacttat cgtcatcgtc cttgtagtca ggcctttcac g                51
```

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      FLAG-tag peptide

<400> SEQUENCE: 11

Asp Tyr Lys Asp Asp Asp Asp Lys
1               5

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccggaattca tgtgtcctca gaagctaacc atc                                 33

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgccaccgc tccctccgcc accggaacct ccccgccgg atcggaccct gcagggaac      59

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcggaggga gcggtggcgg aggttcgagg gtcattccag tctctggacc t             51

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcacctcca tcagcgcttc cggcggagct cagatagcc                           39

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccggaagcg ctgatggagg tgaggtgcag ctgttggagt c                        41

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
aaggaaaaaa gcggccgcct atttgtcatc atcgtctttg tagtc          45

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
actcagtaag gcggccgcct attacttatc gtcatcgtcc ttgtagtc       48

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tccgtctaga tcagcgctgc ctttgatttc caccttggtc ccttg          45

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ggcagcgctg atctagacgg atgttactgc cacggcacag tcattgaaag c   51

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
atcgtcatcg tccttgtagt cgcagcgact cctttccgc tt              42

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
aaatccggat ccgcgggatg ttactgccac ggcacagtc                 39

```
<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23 gatggggaa ttcttggttc atccggatgt tactgccacg gcacagtcat tgaa          54

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggatgaacca agaattcccc catcgccgca gcgactcctt ttccgctt                48

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gccattttcc aacagcacaa ataacgggtt                                    30

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gatgatggtc gacggcgcta ttcag                                         25

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide coding a 5 amino acid linker

<400> SEQUENCE: 27
tccggatccg cggga                                                    15

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide coding a 5 amino acid linker

<400> SEQUENCE: 28
aaatccggat ccgcgggatg t                                             21

<210> SEQ ID NO 29
```

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide coding a 10 amino acid linker

<400> SEQUENCE: 29
ggcgatgggg gaattcttgg ttcatccgga                                      30

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide coding a 10 amino acid linker

<400> SEQUENCE: 30
tgcggcgatg ggggaattct tggttcatcc ggatgt                               36

<210> SEQ ID NO 31
<211> LENGTH: 75
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ctcgaattct cttcctcatc gggtagtagc tcttccggct catcgtccag cggcctcaga    60
tcatcttctc aaaat                                                     75

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ctcgcggccg ctcatcacag agcaatgact ccaaagta                             38

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Ser Ser Ser Ser Gly
1               5

<210> SEQ ID NO 34
<211> LENGTH: 116
<212> TYPE: PRT
<213> ORGANISM: Artificial Sequence
<220> FEATURE:
<223> OTHER INFORMATION: Description of Artificial Sequence: Synthetic L19 VH polypeptide

<400> SEQUENCE: 34

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      L19 VL polypeptide

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
50                      55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105
```

COMPOSITIONS AND METHODS FOR TREATMENT OF ANGIOGENESIS IN PATHOLOGICAL LESIONS

This application is a divisional of U.S. application Ser. No. 10/204,581, filed Aug. 22, 2002, which is a national phase of PCT/IB01/00382, filed Feb. 22, 2001, which claims the benefit of priority of U.S. provisional application Nos. 60/184,767, filed Feb. 24, 2000 and 60/257,192, filed Dec. 21, 2000.

REFERENCE TO SEQUENCE LISTING

This application contains a Sequence Listing submitted in electronic and print form. The electronic and print form of the Sequence Listing are identical to each other pursuant to 37 CFR §1.52(e)(4), contains the following file: "PHILO5D1.txt", having a size in bytes of 10,714 bytes, recorded on Apr. 30, 2012. The information contained in the sequence listing is hereby incorporated by reference in its entirety pursuant to 37 CFR §1.52(e)(5).

The present invention relates to treatment of lesions of pathological angiogenesis, especially tumors, rheumatoid arthritis, diabetic retinopathy, age-related macular degeneration, and angiomas. Aspects of the present invention employ a conjugate or fusion of a molecule that exerts a biocidal or cytotoxic effect on target cells in the lesions and an antibody directed against an extracellular matrix component which is present in such lesions. In preferred embodiments, the antibody is directed against fibronectin ED-B. Preferred embodiments of the biocidal or cytotoxic molecule include interleukin-2 (IL-2), doxorubicin, interleukin-12 (IL-12), Interferon-γ (IFN-γ), Tumor Necrosis Factor α (TNFα) also, especially with the L19 antibody (see below), tissue factor (preferably truncated). By targeting bioactive molecules to an extracellular matrix component, killing of target cells may be achieved.

Tumors cannot grow beyond a certain mass without the formation of new blood vessels (angiogenesis), and a correlation between microvessel density and tumor invasiveness has been reported for a number of tumors (1). Molecules capable of selectively targeting markers of angiogenesis create clinical opportunities for the diagnosis and therapy of tumors and other diseases characterized by vascular proliferation, such as rheumatoid arthritis, diabetic retinopathy and age-related macular degeneration (2-8).

The ED-B domain of fibronectin, a sequence of 91 amino acids identical in mice, rats and humans, which is inserted by alternative splicing into the fibronectin molecule, specifically accumulates around neovascular structures and represents a target for molecular intervention (9-11). Using a human recombinant antibody (L19) to the ED-B domain the possibility of in vivo neovasculature targeting has been demonstrated in different tumor models (12,13).

The present invention is based on the inventors' experimental work employing an antibody directed against the ED-B domain of fibronectin, found in angiogenesis in pathological lesions such as tumors, conjugated with molecules that exert biocidal or cytotoxic effects on target cells. Some such molecules may interact with a membrane-bound receptor on the target cell or perturb the electrochemical potential of the cell membrane. Exemplary molecules demonstrated experimentally herein include interleukin-2 (IL-2), tissue factor, doxorubicin, interleukin-12 (IL-12), Interferon-γ (IFN-γ) and Tumor Necrosis Factor α (TNFα).

Interleukin-2 (IL-2), a four α helix bundle cytokine produced by T helper 1 cells, plays an essential role in the activation phases of both specific and natural immune responses (14). IL-2 promotes proliferation and differentiation of activated T and B lymphocytes and of natural killer (NK) cells, and induces cytotoxic T cell (CTL) activity and NK/lymphokine activated killer (LAK) antitumor cytotoxicity. IL-2 has been used in immunotherapy approaches of several human tumors (15). Administration of recombinant IL-2 (rIL2) alone or in combination with adoptively transferred lymphoid cells has resulted in the regression of established tumors in both animal models and patients. However, its in vivo therapeutic efficacy is limited by its rapid clearance and, at high doses, by a severe toxicity mainly related to a vascular leak syndrome (16). Delivery of IL-2 to the tumor site by means of an antibody directed against a cell-surface tumor marker may allow achievement of active local concentrations of IL-2, as well as reducing toxicities associated to systemic administration (17).

In certain embodiments, the present invention diverges in a novel and unobvious way from the referenced prior art by conjugating IL-2 to an antibody directed to an extracellular matrix component, which component is present in angiogenesis in pathological lesions. As noted, in the prior art attempts to employ IL-2 in treatment of tumors by delivery using an antibody, the antibody has been directed against a cell-surface tumor marker. However, tumor cells present a great heterogeneity in expression of cell surface tumor markers, and may be down-regulated during therapies.

The presence of IL-2 bound at a tumor cell surface results in activation and/or targeting of effector cells of the immune system, either $CD8^+$ cytotoxic T cells or natural killer (NK) cells, and in the induction of an efficient anti-tumor immune response. T or NK cells receive one signal through receptor(s) (for instance T-cell receptor for T cells) specifically recognizing appropriate ligands at the tumor cell surface, and a second signal through IL-2 receptor chains by IL-2, also localized at the tumor cell surface (Lode et al., 1999, *PNAS USA*, 96: 8591-8596 and references therein).

Differently, in the experiments described in more detail below, the inventors constructed and expressed in mammalian cells an antibody-IL2 fusion protein, the antibody (L19, of which the sequence is disclosed in Pini et al. (1998) *J. Biol. Chem.* 273: 21769-21776) being directed against a component of the extracellular matrix present in angiogenesis in pathological lesions (in particular fibronectin ED-B). In vivo biodistribution experiments in tumor bearing mice demonstrated accumulation of the fusion protein around new forming tumor blood vessels. The fusion protein was tested in therapeutic experiments in tumor bearing animals and surprisingly found to induce an antitumor effect and to be significantly more active in reducing tumor growth than an equimolar mixture of L19 and IL-2.

Tissue factor is a component of the blood coagulation cascade, normally present in a membrane-anchored form in the adventitia of blood vessels and therefore not accessible to other components of the blood coagulation cascade. When blood vessels are damaged (e.g. in a wound), tissue factor becomes accessible and, upon binding to Factor VIIa, starts a series of biochemical processes which result in blood clot formation. The truncated form of TF (residues 1-219) is significantly less active in promoting blood coagulation and can therefore be injected systemically either alone, or bound to a monoclonal antibody.

Thorpe and colleagues have demonstrated in an artificial system the principle of selective intraluminal blood coagulation in tumoral blood vessels, resulting in tumor infarction and subsequent tumor cell death (X. Huang et al. (1997) *Science*, 275, 547-550). The authors subcutaneously implanted tumor cells, engineered to secrete interferon gamma and therefore to up-regulate MHC-II expression on the luminal surface of surrounding (tumoral) blood vessels. By doing so, they created an artificial marker of angiogenesis which could be used for molecular intervention. The authors then injected these tumor-bearing mice with bispecific antibodies, capable of simultaneous binding to a truncated form of tissue factor (TF) and to MHC-II, precomplexed with TF. This macromolecular complex (Acoaguligand@) mediated the rapid tumor infarction and complete remission in some of the tumor-bearing mice treated.

In a second experimental system, Thorpe and colleagues used as therapeutic agent a monoclonal antibody specific for the vascular cell adhesion molecule-1 (VCAM-1), chemically cross-linked to TF (Ran et al. (1998) *Cancer Res.*, 58, 4646-4653). As tumor model, the authors chose SCID mice bearing a human L540 Hodgkin's tumors. A 50% reduction in tumor growth rate was observed. Based on their observations, the authors concluded that the selective thrombotic action on tumor and not normal cells resulted from a requirement for coincident expression of the target molecule VCAM-1 and PS on the tumor endothelial cell surface. This provided expectation that the selective thromobotic action would occur only if coaguligands are delivered to the luminal side of new blood vessels and only if these blood vessels display PS on their luminal side.

U.S. Pat. No. 6,004,555 and U.S. Pat. No. 5,877,289 describe work by Thorpe with tissue factor.

The present inventors have now found that tissue factor delivered to the extracellular matrix of pathological lesions, e.g. tumors, is surprisingly able to mediate a biocidal effect (e.g. on tumor cells), specifically infarction, especially when fused to an L19 antibody molecule (see below). In accordance with the present invention, tissue factor (preferably truncated as is known in the art) is provided as a conjugate or fusion with a specific binding member directed to a component of the extracellular matrix found in lesions of pathological angiogenesis, e.g. fibronectin ED-B or tenascin-C.

Doxorubicin (doxo) is one of the most effective anti-cancer drugs used to treat cancer and one of a few chemotherapeutic agents known to have antiangiogenic activity. However, doxorubicin has no cytotoxic activity when bound to antibodies directed against tumor-associated markers on the cell membrane which do not internalise (Chari (1998) *Advanced Drug Delivery* 31, 89-104). Conjugates of doxorubicin and a rapidly internalising antibody directed against tumour-associated markers expressed on the surface of tumour cells have been shown to have an anti-tumour effect (R. V. J. Chari, 1998).

The present inventors have, differently, targeted doxorubicin to the extracellular matrix of lesions, e.g. tumors, by conjugation with a specific binding member directed against a component of the extracellular matrix. In a preferred embodiment demonstrated experimentally herein, the inventors conjugated doxorubicin to an antibody fragment directed against fibronectin ED-B by means of a cleavable linker, allowing for slow release of the doxorubicin. The experiments demonstrate a therapeutic effect. Unlike other approaches, this cleavage occurs in the extracellular milieu, and does not rely on internalisation and/or proteolytic cleavage.

IL-12 is a heterodimeric protein composed of a 40 kD (p40) subunit and a 35 kD (p35) subunit. IL-12 is produced by macrophages and B lymphocytes and has been shown to have multiple effects on T cells and natural killer (NK) cells. Some of these IL-12 activities include the induction of interferon gamma in resting and activated T and NK cells, the enhancement of cytotoxic activity of NK and T cells, and the stimulation of resting T cell proliferation In the presence of a comitogen. Current evidence indicates that IL-12 is a key mediator of cellular immunity. Based on its activity, it has been suggested that IL-12 may have therapeutic potential as a vaccine adjuvant that promotes cellular-immunity and as an anti-viral and anti-tumor agent. In fact, IL-12 is currently being evaluated as an anti-cancer drug in Phase I/II clinical trails (Genetics Institute, Cambridge Mass.). However, in the phase II clinical study administration of recombinant human IL-12 (rhIL-12) resulted in severe toxicity (Atkins et. Al, 1995). This has, so far, hampered its further development. In this context, it appears that developing strategies for locally constricted delivery of the cytokine to the tumor could reduce the problems related to toxicity in clinical applications.

Single peptide chain p40-p35 fusions (Lieschke et. al, 1997) retain specific in vivo activity, comparable to that of native and recombinant IL-12. The present inventors have constructed a single polypeptide fusion protein of the murine p35-p40 genes with the antibody L19, directed against the ED-B domain of fibronectin, a component of the extracellular matrix and a marker of angiogenesis. By an in vitro assay (T cell proliferation assay) it was demonstrated that the IL-12-L19 fusion protein retained IL-12 activity comparable to commercially available IL-12. Furthermore, in vivo biodistribution experiments in mice proved accumulation of the fusion protein in tumors.

IL-12 has been supposed to act at the cell surface level. Thus, it was not predictable that depositing and enriching it in the tumoral extracellular matrix (ECM) would have any effect on the rate of tumor growth. In therapeutic experiments, however, the fusion protein was found to induce anti-tumor effects comparable to the ones obtained with the L19-IL2 fusion protein by significantly reducing tumor growth in tumor bearing mice.

Interferon gamma (IFN-γ) is a pleiotropic cytokine that plays a central role in promoting innate and adaptive mechanisms of host defence. It is now well recognised that IFN-γ, a non-covalently associated homodimeric cytokine, exerts its biologic effects by interacting with an IFN-γ receptor that is ubiquitously expressed on nearly all cells. Functionally active IFN-γ receptors consist of two distinct subunits: a 90-kDa receptor alpha chain and a 62-kDa receptor beta chain. The physiologic role of IFN-γ in promoting host resistance to infectious organisms is unequivocal (Newport et al. (1996) *New Engl. J. Med.*, 335, 1941-1949; Jouanguy et al. (1996) *New Engl. J. Med.*, 335, 1956-1961).

In contrast, the role that IFN-γ plays in the development of host anti-tumor responses is less well established. IFN-γ plays a critical role in promoting rejection of transplantable tumors. Furthermore, endogenously produced IFN-γ forms the basis of a tumor surveillance system that controls development of both chemically induced and spontaneously arising tumors in mice.

Considering that production of IFN-γ makes a tumor immunogenic, it is tempting to speculate that decorating a tumor with IFN-γ (for example, by means of IFN-γ-antibody fusion proteins) may lead to an anti-tumor response. Systemically administered unconjugated IFN-γ has been studied in multi-centre clinical trials in patients with cancer, with very modest response rates. However, recent indication of clinical usefulness of intraperitoneal applications of IFN-γ in patients with ovarian cancer has become available from a Phase III clinical trial (Windbichler et al. (2000) *Br. J. Cancer*, 82, 1138-1144).

The present inventors have found that when targeting the L19-interleukin-12 fusion protein to tumor vasculature in tumor bearing mice, they have observed increased levels of IFN-γ in the blood. In contrast, no elevated levels of IFN-γ could be detected with a non-targeted scFv-interleukin-12 fusion protein.

Tumor Necrosis Factor α (TNFα) is a cytokine produced by many cell types, mainly activated monocytes and macrophages. It is expressed as a 26 kDa integral transmembrane precursor protein from which a mature protein of approximately 17 kDa is released by proteolytic cleavage. The soluble bioactive TNFα is a homotrimer that interacts with two different cell surface receptors (Tartaglia L. A., et al *J. Biol. Chem.*, 268: 18542-18548, 1993) p55TNFR (50-60 kDa) and p75TNFR (75-80 kDa). p75TNFR is species-specific; in fact, human TNFα does not bind to this mouse receptor.

TNFα can induce hemorrhagic necrosis of transplanted solid tumors, in vivo (Carswell E. A., et al, *Proc. Natl. Acad. Sci. USA*, 72: 3666-3670, 1975), and can exert cytotoxic activity in vitro against some tumor cell lines (Helson L., et al, *Nature*, 258: 731-732. 1975).

The anti-tumor efficiency of TNFα in some animal models fostered hopes of its possible use as a therapeutic agent in human cancer. Clinical trials performed to demonstrate the anti-tumor efficacy of TNFα, however, showed that systemically administered therapeutically effective doses were accompanied by unacceptably high levels of systemic toxicity, hypotension being the most common dose-limiting toxic effect. Moreover, TNFα has a very rapid clearance from the bloodstream (plasma half-life generally less than 30 minutes) (Blick M. m et al. *Cancer Res.*, 47: 2989, 1987), which decreases the hematic concentration under therapeutic levels, very rapidly. Good clinical results have been achieved in humans only in loco-regional treatments of non disseminated tumors (e.g., isolated-limb-perfusion for sarcoma and melanoma) (Franker D. L., et al, *Important Adv. Oncol.* 179-192, 1994.)

The anti-tumor activity of TNFα in many animal models seems to be due to a combination of a direct toxic effect (in B combination with tumor-derived factors that synergise with TNFα) on endothelial cells of the growing tumor vasculature (Clauss M., et al. *J. Biol. Chem.*, 265:7078-7083, 1990a), as well as to alterations of the hemostatic properties of proliferating endothelial cells in tumor angiogenesis (Clauss., et al *J. Exp. Med.*, 172:1535-1545, 1990b). There is also evidence of a direct cytotoxic effect on tumor cells. Indirect (host-mediated) effects of TNFα, such as the induction of T cell-dependent immunity, can contribute to tumor regression on animal models (Palladino Jr. M. A., et al. *J. Immunol.*, 138:4023-4032, 1987).

In the experiments described below, the inventors constructed and expressed on mammalian cells an antibody-murine TNFα (mTNFα) fusion protein, the antibody L19 being directed against a component of the ECM present in angiogenesis in pathological lesions (in particular B-FN). In vivo biodistribution experiments in tumor-bearing mice demonstrated accumulation of the fusion protein around new forming tumor blood vessels. The fusion protein was tested in therapeutic experiments in tumor bearing animals and surprisingly was found to induce an anti-tumor effect and to be active in reducing tumor growth.

BRIEF DESCRIPTION OF THE FIGURES

FIG. 19 discloses SEQ ID NO: 28.

FIG. 20 discloses SEQ ID NO: 30.

FIG. 21 discloses "SSSSG" as SEQ ID NO: 33.

Figure 1:
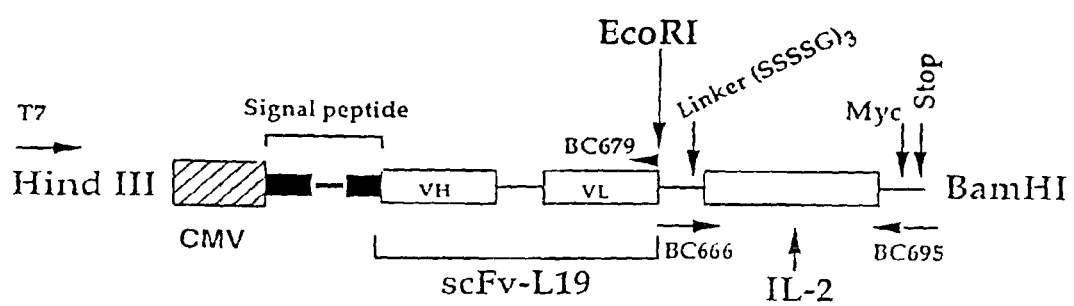
FIG. 1 shows a schematic representation of the scFv L19-IL2 cDNA construct. scFv-L19 and IL2 cDNA were genetically fused with a DNA linker (---) encoding for 15 amino acids (SSSSG)$_3$ (SEQ ID NO: 1) and cloned into the pcDNA3 mammalian expression vector using the HindIII and BamHI restriction sites. The hatched box represents the CMV promoter sequence, the filled box the genomic sequence of the signal secretion leader peptide (■ intron inside of the genomic sequence) and white boxes the VH or VL of scFV-L19 and IL2 sequence. T7, BC666, BC679 and BC695 are primers used in the PCR amplifications described in Materials and Methods.
Figure 2:
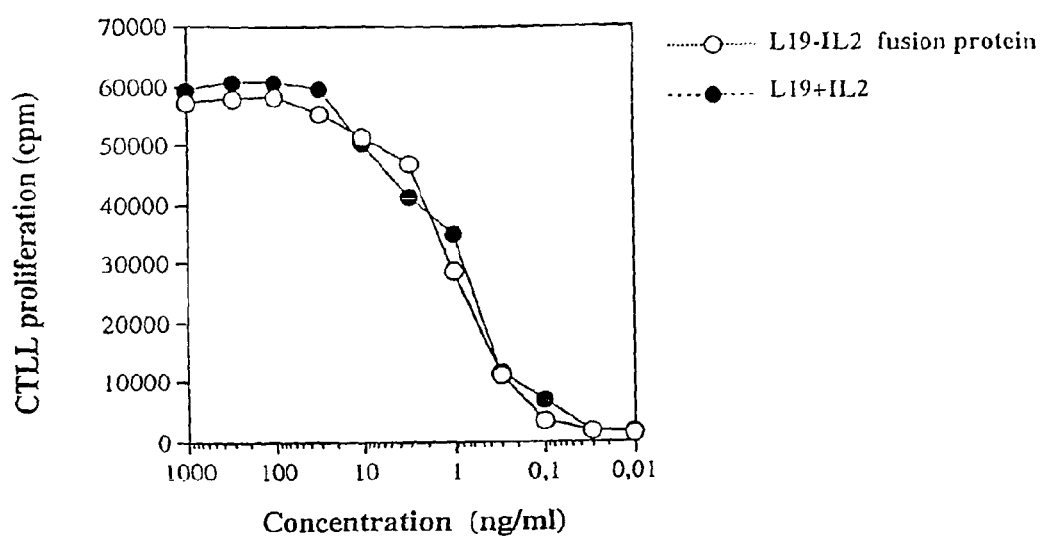
FIG. 2 shows biological activity of the IL2 portion of the fusion protein (○) and of IL2 contained in a mixture of equimolar concentrations of L19 and IL2 (●) measured by CTLL cell proliferation.

All documents cited herein are incorporated by reference.

The present invention provides for treatment of lesions of pathological angiogenesis.

In one aspect the invention provides a method of treating angiogenesis in pathological lesions, the method comprising administering a conjugate of (i) a molecule which exerts a biocidal or cytotoxic effect on target cells by cellular interaction and (ii) a specific binding member specific for an extracellular matrix component which is present in angiogenesis in pathological lesions.

In another aspect, the invention provides the use of a conjugate of (i) a molecule which exerts a biocidal or cytotoxic effect on target cells by cellular interaction and (ii) a specific binding member specific for an extracellular matrix component which is present in angiogenesis in pathological lesions, in the manufacture of a medicament for treatment of pathological angiogenesis.

In a further aspect the invention provides a conjugate of (i) a molecule which exerts a biocidal or cytotoxic effect on target cells by cellular interaction and (ii) a specific binding member specific for an extracellular matrix component which is present in angiogenesis in pathological lesions, for use in a method of treatment of the human or animal body by therapy. Such treatment may be of pathological lesions comprising angiogenesis.

A still further aspect of the invention provides a conjugate of (i) a molecule which exerts a biocidal or cytotoxic effect on target cells by cellular interaction and (ii) a specific binding member specific for an extracellular matrix component which is present in angiogenesis in pathological lesions. Such a conjugate preferably comprises a fusion protein comprising the biocidal or cytotoxic molecule and a said specific binding member, or, where the specific binding member is two-chain or multi-chain, a fusion protein comprising the biocidal or cytotoxic molecule and a polypeptide chain component of said specific binding member. Preferably the specific binding member is a single-chain polypeptide, e.g. a single-chain antibody molecule, such as scFv. Thus a further aspect of the present invention provides a fusion protein comprising the biocidal or cytotoxic molecule and a single-chain Fv antibody molecule specific for an extracellular matrix component which is present in lesions comprising angiogenesis, especially a tumor-associated extracellular matrix component. As discussed, in a preferred embodiment the component allowing for discriminatory targeting of extracellular matrix of pathological lesions compared with normal is fibronectin ED-B. In another preferred embodiment the component is the C domain of tenascin-C (Carnemolla et al. (1999) Am. J. Pathol., 154, 1345-1352]).

The biocidal or cytotoxic molecule that exerts its effect on target cells by cellular interaction, may interact directly with the target cells, may interact with a membrane-bound receptor on the target cell or perturb the electrochemical potential of the cell membrane. Molecules which interact with a membrane-bound receptor include chemokines, cytokines and hormones. Compounds which perturb the electrochemical potential of the cell membrane include hemolysin, ionophores, drugs acting on ion channels. In exemplary preferred embodiments the molecule is interleukin-2, tissue factor (preferably truncated) or doxorubicin. Other embodiments may employ interleukin 12, interferon-gamma, IP-10 and Tumor Necrosis Factor-α (TNF-α).

As discussed further below, the specific binding member is preferably an antibody or comprises an antibody antigen-binding site. Conveniently, the specific binding member may be a single-chain polypeptide, such as a single-chain antibody. This allows for convenient production of a fusion protein comprising single-chain antibody and the biocidal or cytotoxic molecule (e.g. interleukin-2 or tissue factor). In other embodiments, an antibody antigen-binding site is provided by means of association of an antibody VH domain and an antibody VL domain in separate polypeptides, e.g. in a complete antibody or in an antibody fragment such as Fab or diabody. Where the specific binding member is a two-chain or multi-chain molecule (e.g. Fab or whole antibody, respectively), the biocidal or cytotoxic molecule may be conjugated as a fusion polypeptide with one or more polypeptide chains in the specific binding member.

The specific binding member may be specific for fibronectin ED-B, or the C domain of tenascin-C.

An antibody antigen-binding site used in a specific binding member in accordance with the present invention may include the VH and/or VL domains of the antibody L19 or an antibody that competes with L19 for binding to ED-B. The L19 VH (EVQLLESGGGLVQPGGSLRLSCAASG-FTFSSFSMSWVRQAPGKGLEWVSSISGSSGT TYY-ADSVKGRFTISRDNSKNTLYLQMNSL-RAEDTAVYYCAKPFPYFDYWGQGTLVT VSS (SEQ ID NO: 34)) and L19 VL (EIVLTQSPGTLSLSPGER-ATLSCRASQSVSSSFLAWYQQK-PGQAPRLLIYYASSRATGI PDRFSGSGSGTDFTLTISR-LEPEDFAVYYCQQTGRIPPTFGQGTKVEIK (SEQ ID NO: 35)) domain sequences are disclosed in Pini et al. (1998) J. Biol. Chem. 273: 21769-21776. The DNA encoding antibody scFvL19 has been deposited on Sep. 25, 2008, in ATCC (Manassas, Va.), and has accession no. PTA-9529.

Other non-antibody specific binding members which may be conjugated with IL-2, TF, doxo, IL-12, IFN-γ or TNF-α or other biocidal or cytotoxic molecules and used in accordance with the present invention include peptides, aptamers and small organic molecules able to interact with a component of the ECM associated with pathological lesions.

As noted, preferably the specific binding member is conjugated with the biocidal or cytotoxic molecule by means of a peptide bond, i.e. within a fusion polypeptide comprising said molecule and the specific binding member or a polypeptide chain component thereof. See Taniguchi et al. (1983) *Nature* 302, 305-310; Maeda et al. (1983) *Biochem. Biophys. Res. Comm.* 115: 1040-1047; Devos et al. (1983) *Nucl. Acids Res.* 11: 4307-4323 for IL-2 sequence information useful in preparation of a fusion polypeptide comprising IL-2. Sequence information for truncated tissue factor is provided by Scarpati et al. (1987) *Biochemistry* 26: 5234-5238, and Ruf et al. (1991) *J. Biol. Chem.* 226: 15719-15725. Other means for conjugation include chemical conjugation, especially cross-linking using a bifunctional reagent (e.g. employing ADOUBLE-REAGENTS™@ Cross-linking Reagents Selection Guide, Pierce).

Where slow release is desirable, e.g. where the biocidal or cytotoxic molecule is doxorubicin or other molecule which perturbs the electrochemical potential of the cell membrane, chemical conjugation may be by means of formation of a Schiff base (imine) between a primary amino group of the specific binding member (a polypeptide such as an antibody or antibody fragment) and an oxidised sugar moiety (daunosamine) of the biocidal or cytotoxic molecule such as doxorubicin.

The lesion treated may be a tumor, including without limitation any one or more of the following: melanoma, neuroblastoma, colorectal carcinoma, renal carcinoma, lung, carcinoma, lung metastasis, breast carcinoma, high-grade astrocytoma (grade III, grade IV), meningioma, angioma.

The lesion may be ocular, e.g. arising from age-related macular degeneration, in which angiogenesis arises from choroidal vessels.

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other.

Antibody

This describes an immunoglobulin whether natural or partly or wholly synthetically produced. The term also covers any polypeptide or protein having a binding domain which is, or is substantially homologous to, an antibody antigen-binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member having an antibody antigen-binding domain binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Antigen Binding Domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members, will generally be employed in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

As noted, where an antibody antigen-binding domain directed against fibronectin ED-B is to be employed in embodiments of the present invention, a preferred such domain comprises the L19 antibody VH and VL domains. Modified forms of one or other of these domains may be employed in further embodiments, e.g. the L19 VH or L19 VL domain in which 1, 2, 3, 4 or 5 amino acid substitutions have been made in a CDR, e.g. CDR3, and/or FR, which specific binding members retain ability to bind fibronectin ED-B. Such amino acid substitutions are generally "conservative", for instance substitution of one hydrophobic residue such as isoleucine, valine, leucine or methionine for another, or the substitution of one polar residue for another, such as arginine for lysine, glutamic for aspartic acid, or glutamine for asparagine. At certain positions non-conservative substitutions are allowable.

The present invention further extends to employing a specific binding member which competes with the L19 antibody for binding to fibronectin ED-B. Competition between binding members may be assayed easily in vitro, for example by tagging a specific reporter molecule to one binding member which can be detected in the presence of other untagged binding member(s), to enable identification of specific binding members which bind the same epitope or an overlapping epitope.

In addition to antibody sequences, a specific binding member employed in accordance with the present invention may comprise other amino acids, e.g. forming a peptide or polypeptide, such as a folded domain, or to impart to the molecule another functional characteristic in addition to ability to bind antigen. Specific binding members of the invention may carry a detectable label.

In further aspects, the invention provides an isolated nucleic acid which comprises a sequence encoding a specific binding member as defined above (e.g. wherein the specific binding member or a polypeptide chain component is provided as a fusion polypeptide with the biocidal or cytotoxic molecule), and methods of preparing specific binding members of the invention which comprise expressing said nucleic acids under conditions to bring about expression of said binding member, and recovering the binding member.

The present invention also provides constructs in the form of plasmids, vectors, transcription or expression cassettes which comprise least one nucleic acid as above.

The present invention also provides a recombinant host cell which comprises one or more constructs as above. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

Expression may conveniently be achieved by culturing under appropriate conditions recombinant host cells containing the nucleic acid. Following production by expression a specific binding member may be isolated and/or purified using any suitable technique, then used as appropriate.

In one embodiment, the nucleic acid of the invention is integrated into the genome (e.g. chromosome) of the host cell. Integration may be promoted by inclusion of sequences which promote recombination with the genome, in accordance with standard techniques.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Reff, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

The present invention also provides a method which comprises using a construct as stated above in an expression system in order to express a specific binding member or polypeptide as above.

Specific binding members according to the invention may be used in a method of treatment of the human or animal body, such as a method of treatment (which may include prophylactic treatment) of a disease or disorder in a human patient which comprises administering to said patient an effective amount of a specific binding member of the invention. Conditions treatable in accordance with the present invention are discussed elsewhere herein.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

A composition may be administered alone or in combination with other treatments, either simultaneously or sequentially dependent upon the condition to be treated.

Specific binding members of the present invention, including those comprising an antibody antigen-binding domain, may be administered to a patient in need of treatment via any suitable route, usually by injection into the bloodstream and/or directly into the site to be treated, e.g. tumor. The precise dose will depend upon a number of factors, the route of treatment, the size and location of the area to be treated (e.g. tumor), the precise nature of the antibody (e.g. whole antibody, scFv molecule), and the nature of any detectable label or other molecule attached to the antibody. A typical antibody dose will be in the range 10-50 mg. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine, or anti-emetics.

The present invention provides a method comprising causing or allowing binding of a specific binding member as provided herein to an extracellular matrix component which is present in angiogenesis in pathological lesions. As noted, such binding may take place in vivo, e.g. following administration of a specific binding member, or nucleic acid encoding a specific binding member.

Further aspects and embodiments of the present invention will be apparent to those skilled in the art given the present disclosure. Aspects and embodiments of the invention are illustrated by the following experimental section.

EXPERIMENTAL

Example 1

Construction and In Vivo Anti-Tumor Activity of Antibody-IL2 Fusion

Materials and Methods

Construction and Expression of L19-IL2 Fusion Protein

The L19-IL2 cDNA was constructed by fusion of a synthetic sequence coding for human IL2 to the 3' end of the sequence coding for the scFv L19. The schematic representation of L19-IL2 cDNA construct is shown in FIG. 1. IL2 cDNA was amplified by Polymerase Chain Reaction (PCR) using BC-666 and BC695 primers and, as template, the IL2 cDNA produced by reverse transcriptase-polymerase chain reaction (RT-PCR) starting from RNA of human phytohaemagglutinin (PHA)-activated peripheral blood lymphocytes as described by Meazza et al. 1996 (18).

The forward BC666 primer (sequence:ctcgaattctcttcct-catcgggtagtagctcttccggct-catcgtccagcggcgcacctacttcaagttctaca (SEQ ID NO: 4)) contained the EcoRI restriction enzyme sequence, a 45 bp encoding for by a 15 amino acids linker $(Ser_4-Gly)_3$ (SEQ ID NO: 1) and 21 bases of the mature human IL2 sequence.

The reverse BC-695 primer (sequence: ctcggatccttatcaat-tcagatcctcttctgagatgagtttttgttcagtcagtgttgagatgatgct (SEQ ID NO: 5)) contained the myc sequence (13), two stop codons and the BamHI restriction enzyme sequence.

The scFvL19, which contained in its 5' end the genomic sequence of the signal secretion leader peptide as reported by Li et al. 1997 (19), was amplified by PCR using T7 primer on the vector pcDNA3.1 (Invitrogen, Croningen, The Netherlands) and the BC 679 primer (sequence: CTCGAAT-TCtttgatttccaccttggtcc (SEQ ID NO: 6)) containing 21 bp of the 3' end of L19 and the EcoRI restriction enzyme sequence. The fused gene was sequenced, introduced into the vector pcDNA3.1 containing the Cytomegalovirus (CMV) promoter and expressed in P3U1 cells in the presence of G418 (750 µg/ml, Calbiochem, San Diego, Calif.). Clones of G418-resistant cells were screened for the secretion of L19-IL2 fusion protein by ELISA using recombinant ED-B domain of human Fibronectin (FN) as antigen.

FN Recombinant Fragments, ELISA Immunoassay and Purification of L19-IL2 Fusion Protein Recombinant FN fragments containing the type III homology repeats 7B89 and ED-B were produced as described by Carnemolla et al. 1996 (20). ELISA immunoassay was performed as reported by Carnemolla et al. 1996 (20). The L19-IL2 fusion protein was purified from the conditioned medium of one positive clone using the recombinant human fibronectin fragment 7B89 conjugated to Sepharose, by affinity chromatography as reported by Carnemolla et al. 1996 (20). The size of the fusion protein was analyzed in reducing condition on SDS-PAGE and in native condition by FPLC gel filtration on a Superdex S-200 chromatography column (Amersham Pharmacia Biotech, Uppsala, Sweden).

IL2 Bioassay

The IL2 activity of the L19-IL2 fusion protein was determined using the CTLL mouse cell line, which is known to proliferate in response to human IL2 as described by Meazza et al. 1996, (18). Serial dilutions of L19-IL2 fusion protein and of an equimolar mixture of L19 and recombinant human IL2 (Proleukin, Chiron) at concentrations from 1000 to 0.01 ng/ml were used in the CTLL-2 proliferation assay.

Animals and Cell Lines

Female athymic-nude mice (8-week-old nude/nude CD1 mice, females) were obtained from Harlan Italy (Correzzana, Milano, Italy). F9, a mouse embryonal carcinoma, mouse T cells (CTLL-2) and mouse myeloma cells were purchased from ATCC (American Type Culture Collection, Rockville, Md., USA; N592, human Small Cell Lung Cancer (SCLC) cell line, was kindly provided by Dr. J. D. Minna (National Cancer Institute and Naval Hospital, Bethesda, Md.); C51, a mouse colon adenocarcinoma cell line derived from BALB/c, was kindly provided by Dr. M. P. Colombo (21).

Biodistribution of L19-IL2 Fusion Protein

Purified L19-IL-2 was radiolabeled with iodine-$^{125}$ using the Iodogen method (22) (Pierce, Rockford, Ill.). The immunoreactive radiolabeled L19-IL-2 (more than 90%) was affinity purified on a 7B89/Sepharose chromatography column. Nude mice with subcutaneously implanted F9 murine teratocarcinoma (20,23) were intravenously injected with about 10 µg (4 µCi) of protein in 100 µl saline solution. Three animals were used for each time point. Mice were sacrificed at 3, 6 and 24 hours after injection. The organs were weighed and the radioactivity was counted. All organs and tumors were placed in fixative for histological analysis and microautoradiography. Targeting results of representative organs are expressed as percent of the injected dose per gram of tissue (% ID/g).

In Vivo Treatment with L19-IL2 Fusion Protein

Treatment with purified L19-IL2 fusion protein was performed in groups of six mice each injected subcutaneously with $20 \times 10^6$ of N592 or with $10^6$ of C51 or with $3 \times 10^6$ of F9 cells. Twenty-four hours after N592, F9 and C51 cell injection, 12 µg of L19-IL2 fusion protein were injected into the tail vein of each animal daily for 10-15 days. Similar groups of animals (six per group) were injected with a mixture of L19 (8 µg) and recombinant human IL2 (4 µg, corresponding to (72,000 UI; Proleukin, $18 \times 10^6$ UI, Chiron) and with Phosphate Saline Buffer pH 7.4 (PBS) for the same number of days. At the end of treatment, animals were sacrificed, tumors weighed and organs (lungs, livers, hearts, kidneys) and tumors were placed in fixative for histological analysis.

Microautoradiography Analysis, Immunohistochemistry and Statistical Analysis

Tumor and organ specimens were processed for microautoradiography to assess the pattern of $^{125}$I-L19-IL2 fusion protein distribution within the tumors or organs as described by Tarli et al. 1999 (12). Immunohistochemical procedures were carried out as reported by Castellani et al. 1994 (11). The nonparametric Mann-Whitney test was used to assess the differences in tumor weights between the three different groups of animals (mice treated with L19-IL2 fusion protein, with mixture of L19+IL2 and PBS).

Results

L19-IL2 Construct and Selection of Clones Expressing L19-IL2 Fusion Protein

G418 resistant clones were screened for the antibody specificity of the supernatants for the ED-B sequence by ELISA as previously described. Supernatants of clones showing immunological specificity for the ED-B sequence were tested for IL2 biological activity.

Figure 3:
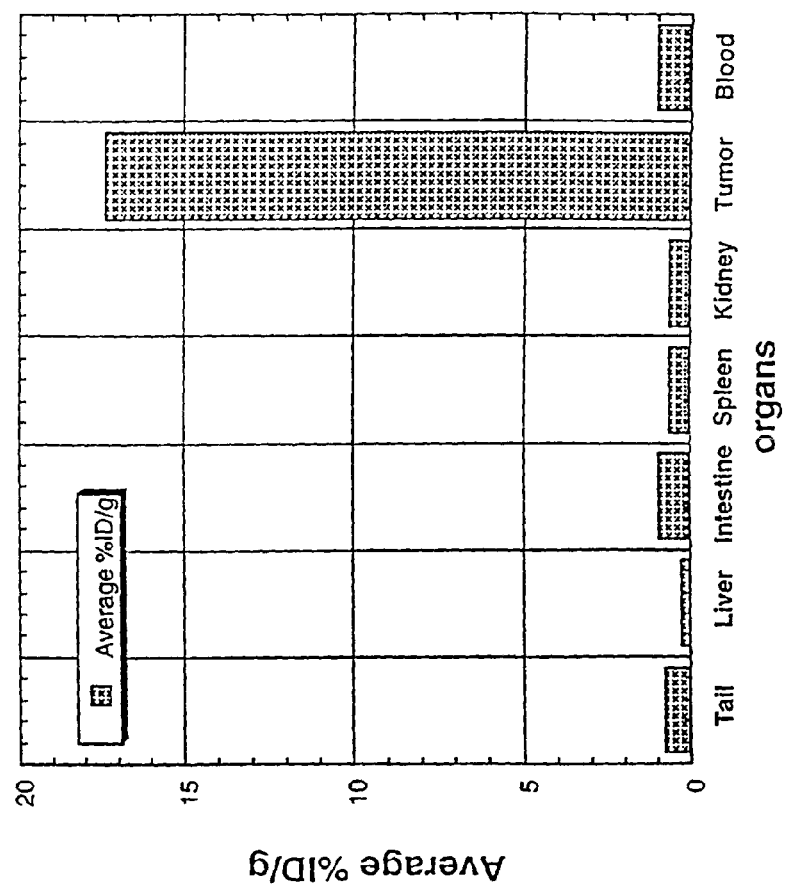
FIG. 3 shows results of a biodistribution analysis performed in mice bearing a subcutaneously-implanted murine F9 teratocarcinoma, injected intravenously with radioiodinated scFv(L19)-TF.

The scFv L19 and the L19-IL2 fusion protein were run on SDS-PAGE. L19-IL2 is purified in a single step by affinity chromatography, contaminations lower than 10% were detectable by SDS-PAGE. The fusion protein showed an apparent molecular mass of about 42 Kd, in line with the expected size of the fusion protein. FPLC analysis of the fusion protein on a S200 Superdex chromatography column (Pharmacia) demonstrated that the protein, in native conditions, is made up of about 70% of dimers and 30% of monomers as previously observed for the scFv L19. Both the immunological activity of the scFvL19 component and the biological activity of the IL-2 component in the purified protein were tested (FIG. 3). Both specific activities were comparable with purified separated molecules.

Biodistribution of Radiolabeled L19-IL2 Fusion Protein in Tumor-Bearing Mice

To investigate whether the L19-IL2 fusion protein was able to efficiently localize in tumoral vessels, as reported for the scFv L19 by Tarli et al. 1999 (12), biodistribution experiments were performed in F9 teratocarcinoma bearing mice.

L19-IL2 fusion protein was shown immunohistochemically to stained strongly blood vessels of glioblastoma tumor. Radioiodinated L19-IL2 fusion protein was injected in the tail vein of mice with subcutaneously implanted F9 tumors, and L19-IL2 fusion protein distribution was obtained at different time points: 3, 6 and 24 hours. Fourteen percent of the injected dose per gram of tissue (% ID/g) localized in the tumor 3 hours after injection as reported in Table 1. The localization of L19-IL2 fusion protein in the tumoral neovasculature was confirmed by microradiographic analysis.

Accumulation of the radiolabeled fusion protein was shown in the blood vessels of the F9 mouse tumor. No accumulation of radiolabeled fusion protein was detected in the vessels of the liver or of other organs of tumor bearing mice.

Treatment of Tumor Bearing Mice with L19-IL2 Fusion Protein

The efficacy of the L19-IL2 fusion protein in suppressing the growth of tumors was tested on three different experimental tumor models: mouse teratocarcinoma, F9; mouse adenocarcinoma, C51 and human small cell lung cancer, N592. For tumor induction, cells of each tumor type, (specifically 20×10$^6$ for N592, 10$^6$ for C51 and 3×10$^6$ for F9) were injected subcutaneously in the animals. Twenty-four hours later animals began receiving daily intravenous injection of either PBS (6 animals), a mixture of L19 and IL2 (6 animals) or L19-IL2 fusion protein (6 animals) for 10-15 days. Twenty-four hours after the last injection the animals were sacrificed, the tumoral mass removed and the tumors weighed.

The results, summarized in Table 2, show a significant decrease in tumor growth in the group of animals treated with L19-IL2 fusion protein with respect both to animals injected with an equimolar mixture of L19 and IL2 proteins and to the third group treated with PBS.

F9 teratocarcinoma tumors were dissected from nude mice after 11 days of intravenous treatments. In L19-IL2 fusion protein treatment group, the tumoral mass grew only in three out of six mice. The non parametric Mann-Whitney test was used to determine the statistical significance of differences in tumor weights between the three groups of animals. The differences in tumor weights between treatment with the fusion protein (L19-IL2), treatment with PBS or a mixture (L19+IL2) were statistically significant (see Table 3).

Example 2

Construction and In Vivo Use of Antibody-Tissue Factor Fusion

Fusion proteins comprising antibody fragments in scFv configuration, genetically fused to truncated tissue factor (scFv-TF), were cloned and expressed. The scFv(L19) as targeting agent specific for the ED-B domain of fibronectin was employed for targeting, and scFv(D1.3) (specific for hen egg lysozyme) as negative control.

The fusion protein scFv(L19)-TF and scFv(D1.3)-TF were expressed in *E. coli* and purified to homogeneity. The antibody moiety was shown to be active by antigen binding assays. The TF moiety was shown to be active using the method of Ruf et al, *J. Biol. Chem.* 226:2158-2166. The ability of scFv (L19)-TF to target solid tumors was shown by quantitative biodistribution analysis, using radioiodinated scFv (L19)-TF injected intravenously in tumor bearing mice (FIG. 3).

The antitumor activity of scFv(L19)-TF and scFv(D1.3)-TF was tested in mice bearing the F9 murine teratocarcinoma, the C51 murine carcinoma or FE8 tumors (derived from subcutaneously implanted ras-transformed rat fibroblasts). Experiments were performed both in mice bearing small tumors and in mice bearing very large tumors.

scFv(L19)-TF, but not scFv(D1.3) or saline, mediated rapid and extensive tumor infarction few hours after injection.

Figure 4:
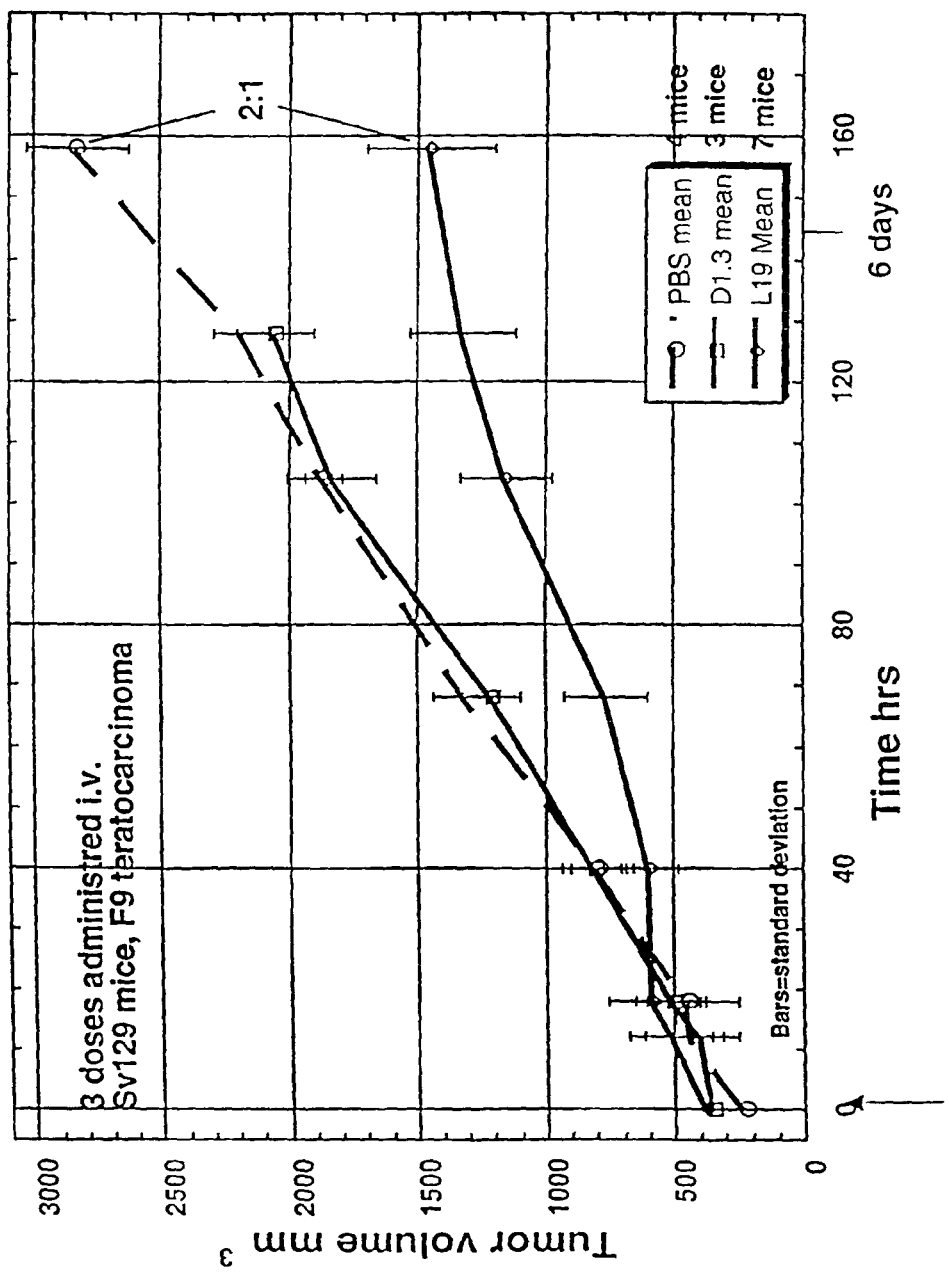
FIG. 4 is a plot (versus time) of the volume of F9 murine teratocarcinoma tumors subcutaneously implanted in mice, which have been injected intravenously with 3 doses of either scFv(L19)-TF or scFv(D1.3)-TF. The first injection (indicated by an arrow) was performed when tumors were small. Standard errors are indicated.
Figure 5:
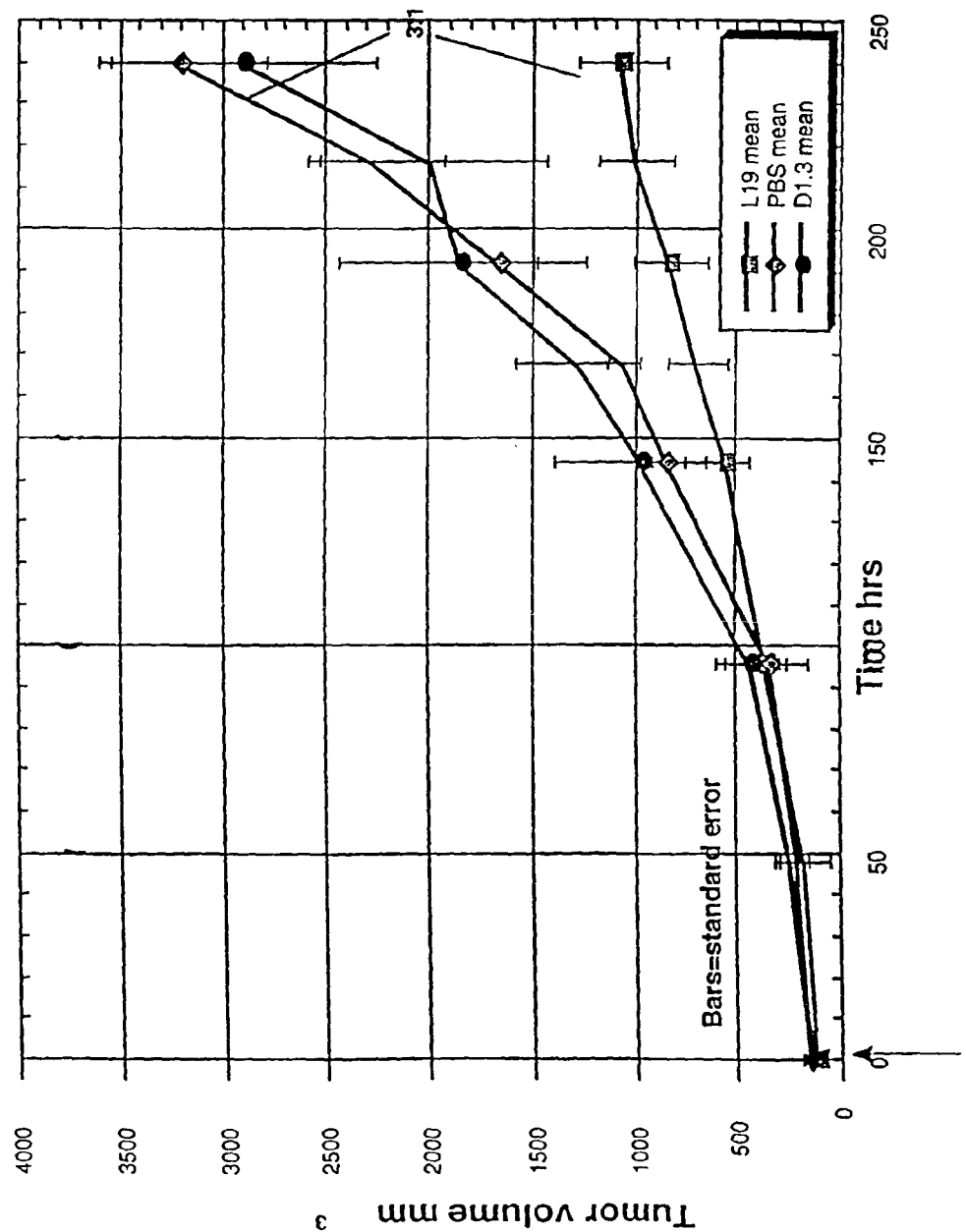
FIG. 5 is a plot (versus time) of the volume of C51 murine carcinoma tumors subcutaneously implanted in mice, which have been injected intravenously with 3 doses of either scFv (L19)-TF or scFv(D1.3)-TF. The first injection (indicated by an arrow) was performed when tumors were small. Standard errors are indicated.
Figure 6:
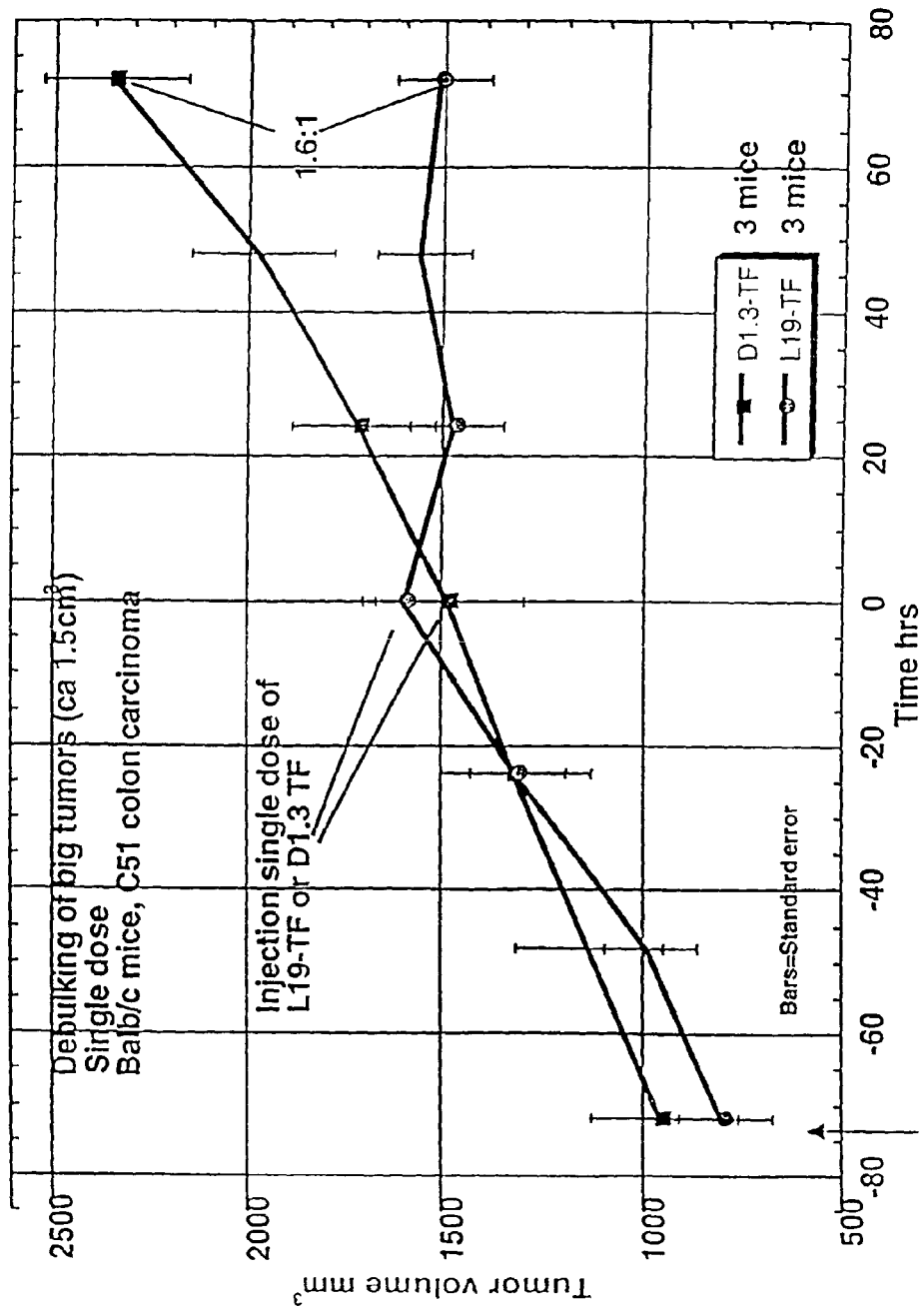
FIG. 6 is a plot (versus time) of the volume of C51 murine carcinoma tumors subcutaneously implanted in mice, which have been injected intravenously with 1 dose of either scFv (L19)-TF (20 μg), scFv(D1.3)-TF (20 μg) or phosphate buffered saline. The injection (indicated by an arrow) was performed when tumors were >1 gram. Standard errors are indicated.
Figure 7:
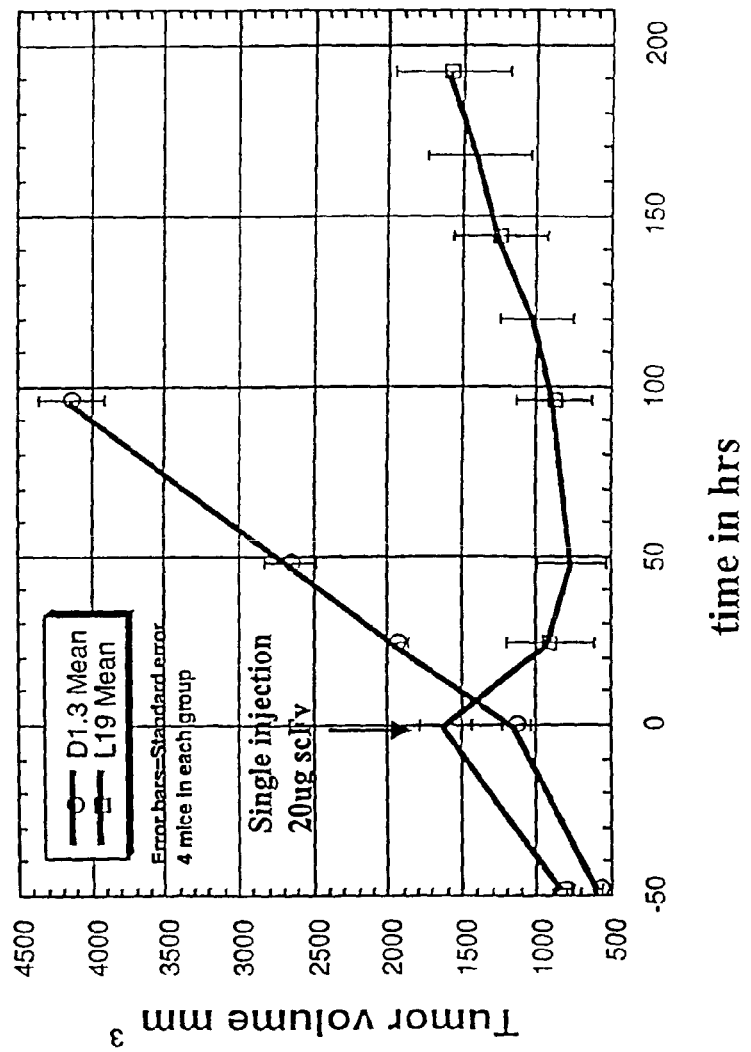
FIG. 7 is a plot (versus time) of the volume of FE8 ras-transformed fibroblast tumors subcutaneously implanted in mice, which have been injected intravenously with 1 dose of either scFv(L19)-TF (20 μg), scFv(D1.3)-TF (20 μg) or phosphate buffered saline. The injection (indicated by an arrow) was performed when tumors were >1 gram. Standard errors are indicated.

Three, injections of 20 μg scFv(L19)-TF resulted in approx. 50% reduction of growth rate in small tumors (FIGS. 4 and 5). In large tumors, one injection of 20 μg scFv(L19)-TF stopped tumor growth, by turning the majority of the tumor into a black and crusty mass (FIGS. 6 and 7). By contrast, one injection of 20 μg scFv(D1.3)-TF had no antitumor effect (FIGS. 6 and 7).

Material and Methods

Cloning of scFv(L19)-TF

The scFv(L19)-TF expression vector was constructed by cloning a synthetic DNA sequence, coding for the human TF, at the 3' end of the DNA sequence encoding the human scFv(L19), using the Not1/EcoR1 sites of a derivative of vector pDN5 (D. Neri et al. (1996) *Nature Biotechnology*, 14, 485-490.), in which the scFv(D1.3) gene had been replaced by the scFv(L19) gene. The human TF DNA sequence was purchased from ATCC and modified by PCR as follows:

The primer TF-banot (5'-T GAG TCA TTC GCG GCC GCA GGT GGC GGT GGC TCT GGC ACT ACA AAT ACT GTG GCA-3' (SEQ ID NO: 7)) introduced to the 5'end of the TF DNA sequence a restriction site for the endonuclease Not1. It also introduced a short linker C-terminally of the restriction site consistent of four glycines and a serine (GGGGS (SEQ ID NO: 8)).

The primer TF-fostueco1 (5'-GTC CTT GTA GTC AGG CCT TTC ACG GAA CTC ACC TTT CTC CTG GCC CAT ACA-3' (SEQ ID NO: 9)) introduced to the 3' end of the TF DNA sequence a Stu1 endonuclease restriction site and then the first four residues of the FLAG-tag. It also removed a EcoRI restriction site in the codon for the amino acid 216 in the TF sequence by a silent mutation.

The primer TF-fostueco2 (5'-AGA GAA TTC TTA TTA CTT ATC GTC ATC GTC CTT GTA GTC AGG CCT TTC ACG-3' (SEQ ID NO: 10)) introduced to the 3'end of the product of TF-fostueco1 the rest of the FLAG-tag (DYKDDDDK (SEQ ID NO: 11)), a EcoRI restriction site and finally two stop codons.

Cloning of scFv(D1.3)-TF

The scFv(D1.3)-TF expression vector was constructed in a similar fashion as described above for scFv(L19)-TF. In short, the TF gene was cloned in the Not1/EcoR1 sites of vector pDN5, which already contains the scFv(D1.3) gene.

Expression and Purification of the scFv-TF Fusion Protein

The vectors were introduced in TG1 *Escherichia Coli* cells. Protein expression and purification by affinity chromatography were performed as described for scFv(D1.3) and for scFv(L19) (Neri et al., 1996; Tarli et al. (1999) *Blood*, 94, 192-198). In addition, a purification step by ion exchange chromatography was performed, in order to obtain homogenous protein preparations.

The size of the fusion protein was analyzed in reducing conditions on SDS-PAGE and in native conditions by FPLC gel filtration on a Superdex S-75 (Amersham Pharmacia Biotech, Uppsala, Sweden).

In Vitro Activity of the Recombinant scFv-TF Fusion Protein

The immunoreactivity of the scFv-TF fusion protein was analyzed by ELISA immunoassay, by BIAcore and by affinity chromatography on antigen column, as described (Neri et al., 1996; D. Neri et al. (1997) *Nature Biotechnology*, 15, 1271-1275.; Tarli et al., 1999).

The enzymatic activity of the scFv-TF fusion protein was analyzed using the Spectrozyme FXa assay (American Diagnostica, Pfungstadt, Germany) as described by Ruf et al (1991).

In Vivo Targeting Activity of the Recombinant L19-TF Fusion Protein

The in vivo targeting performance was analysed by biodistribution analysis as described in Tarli et al. (1999). Briefly, purified scFv(L19)-TF fusion protein was radioiodinated and injected into nude mice with subcutaneously implanted F9 murine teratocarcinoma. Mice were sacrificed at 24 hours after injection. The organs were weighed and the radioactivity counted. Targeting results of representative organs are expressed as percent of the injected dose per gram of tissue (% ID/g).

In Vivo Treatment with the Recombinant L19-TF Fusion Protein

Tumor bearing mice were obtained by subcutaneous injection of $10^6$ of FE8 rat fibroblast, C51 colon carcinoma or F9 teratocarcinoma cells (Tarli et al., 1999). The cells were allowed to grow until the tumoral volume could be measured by a slide-calliper.

Mice with tumors of volume ca 200-300 mm$^3$ were injected with 20 ug scFv-TF fusion protein corresponding to 10 ug TF in 200 ul saline. The injection was repeated after 48 and 96 hours. Mice were monitored by tumor volume, weight and appearance including photographic documentation.

Mice with tumors of volume ca 1500 mm$^3$ were injected with a single dose of with 20 ug scFv-TF fusion protein corresponding to 10 ug TF in 200 ul saline. The injection was not repeated. Mice were monitored by tumor volume, weight and appearance including photographic documentation.

Example 3

Construction and In Vivo Use of Antibody-Doxorubicin

A conjugate of the anti-FN ED-B scFv L19 and doxorubicin was constructed. As chemistry for the cleavable linker, the formation of a Schiff base (imine) between a primary amino group of the L19 antibody and the oxidised sugar moiety (daunosamine) of doxorubicin was chosen.

Figure 8:
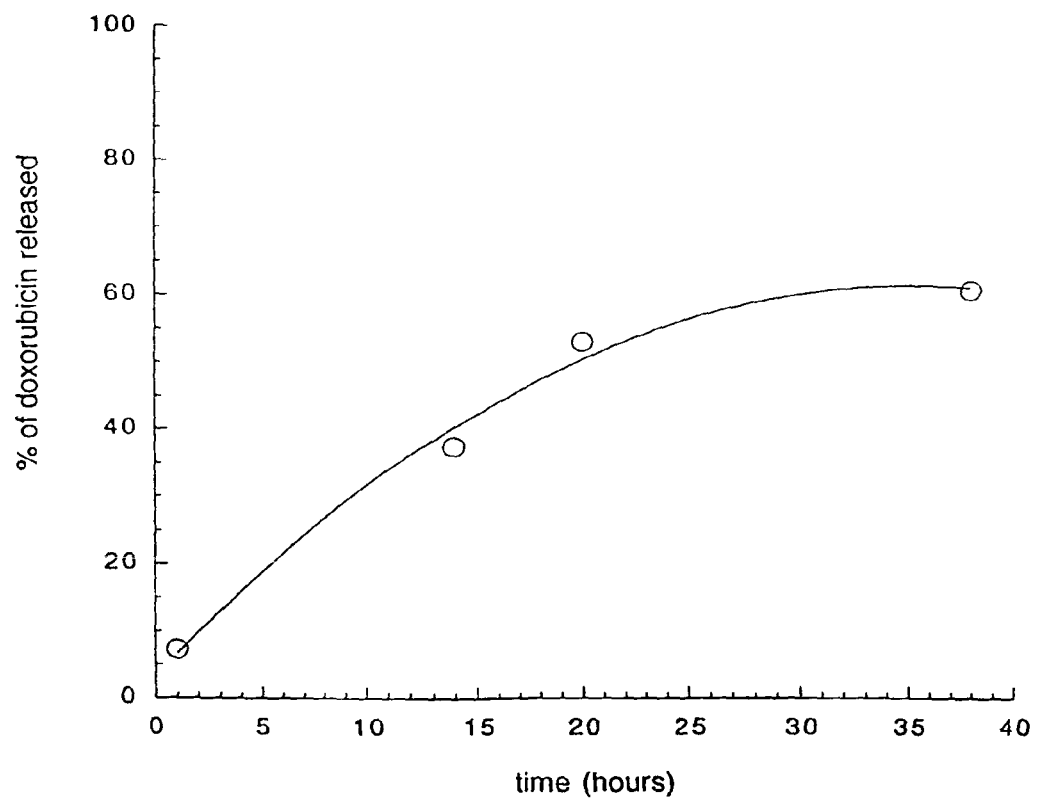
FIG. 8 illustrates the kinetic of doxorubicin release from scFv(L19)-doxorubicin conjugates, analysed by HPLC.

The ability of doxorubicin to be released from scFv(L19) was assayed by HPLC. The half-life of doxorubicin release was approximately 10 hours, at pH 7.4 and 37° C. (FIG. 8).

Figure 9:
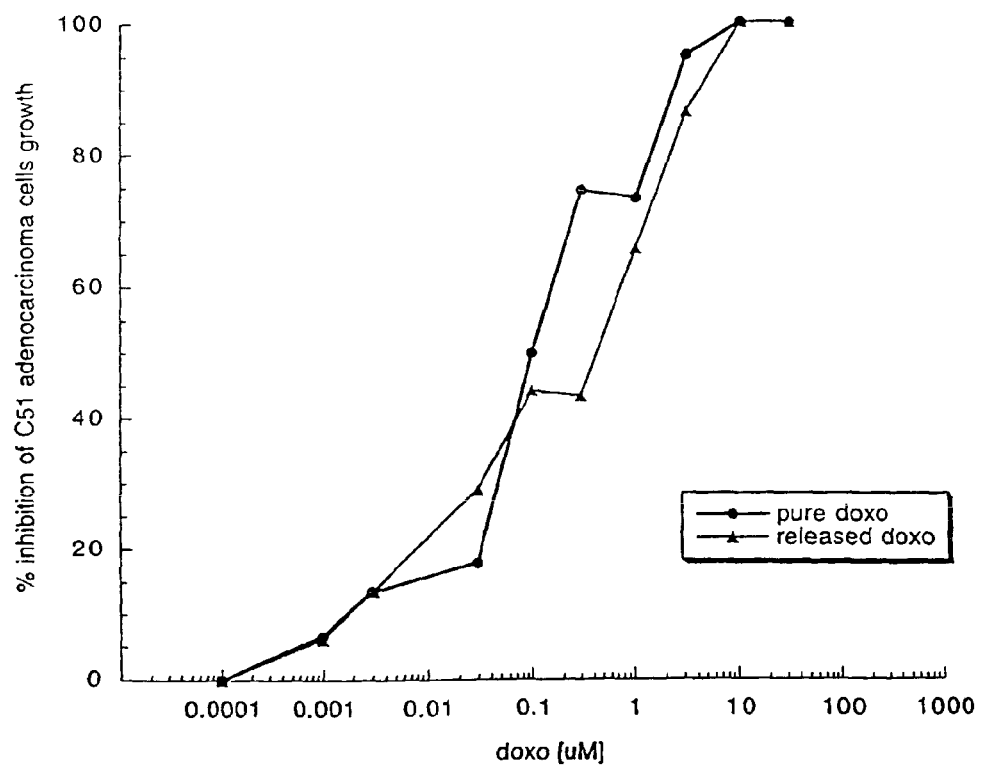
FIG. 9 illustrates the toxicity towards C51 murine carcinoma cells, mediated by doxorubicin released from a scFv (L19)-doxorubicin conjugate.

The ability of released doxorubicin to be taken up by neighboring cells (in vitro) and to mediate a biocidal activity was tested by cytotoxicity assays using C51 murine carcinoma cell line. FIG. 9 shows that both pure doxorubicin and doxorubicin released from scFv(L19)-doxorubicin have 50% inhibitory concentrations towards C51 cells in the 0.1 μM range.

Figure 10:
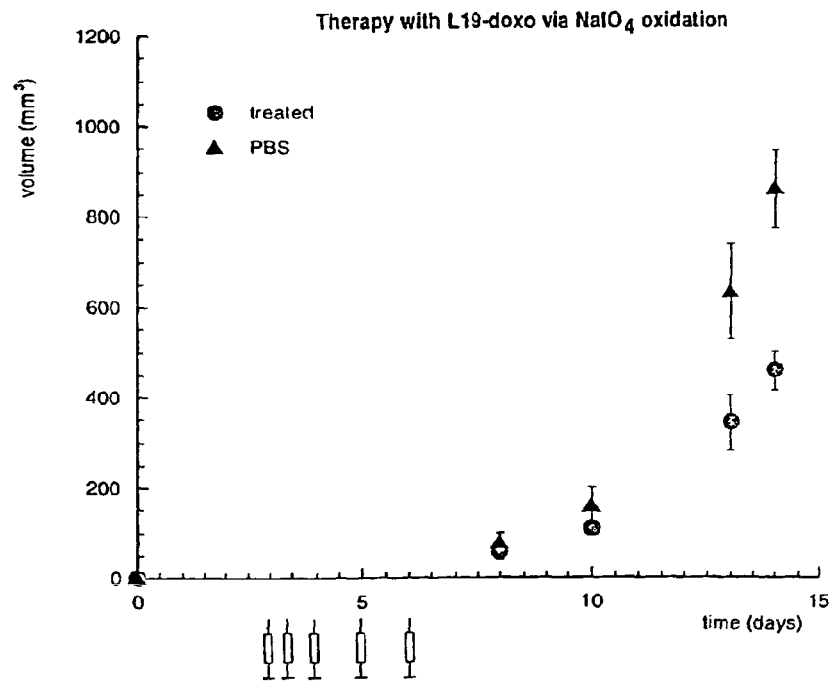
FIG. 10 is a plot (versus time) of the volume of F9 murine teratocarcinoma tumors subcutaneously implanted in mice, which have been injected intravenously with 5 doses of either scFv(L19)-doxorubicin [18 μg/injection] or phosphate buffered saline. The first injection (indicated by an arrow) was performed when tumors were small. Standard errors are indicated.

The anti-tumor activity of scFv(L19)-doxorubicin immunoconjugate was tested in vivo by repeated intravenous injections in mice bearing the subcutaneously implanted C51 murine tumor. Five injections of 18 μg of scFv(L19)-doxorubicin caused a 50% reduction in tumor growth rate, relative to control mice injected with saline (FIG. 10).

Materials and Methods

Conjugation of Doxorubicin to scFv(L19)

The antibody fragment scFv(L19) was prepared as described in Tarli et al. (1999) *Blood*, 94, 192-198.

1 mg of doxorubicin (1.72 μmoles) was mixed with 0.53 mg (2.5 μmoles) NaIO$_4$ in 1 ml phosphate buffer (pH=7.4) and incubated for one hour at room temperature in the dark. 1 μl glycerol 20% was then added in order to consume excess periodate. The solution of oxidized drug was mixed with 1.3 mg (43 nmoles) of scFv(L19) in 0.15 M potassium carbonate buffer (pH=9.5). The formed precipitate was removed by centrifugation (4000 rpm, 1') and the liquid phase was loaded onto a PD-10 disposable gel filtration column.

The molar concentrations of doxorubicin and scFv(L19) were determined from their UV absorption at 496 and 280 nm, respectively, including a correction for the absorption of doxorubicin at 280 nm. The degree of conjugate coupling was calculated as (ScFv:doxo) molar ratio (MR) from the following formula:

$$MR = \{[A^{280}B(0.724 \times A^{496})]/[(1.4)(2.7 \times 10^4)]\}/[A^{496}/(8.03 \times 10^3)]$$

where A indicates the spectrophotometric absorbance; 0.724 is a correction for the doxorubicin absorption at 280 nm; $2.7 \times 10^4$ is the molecular weight of a scFv; 1.4 is the absorbance value at 280 nm of a solution 1 mg/ml of a scFv; $8.03 \times 10^3$ ($M^{-1}$ $cm^{-1}$) is the extinction coefficient of doxorubicin at 496 nm.

Coupling the L19 antibody fragment with doxorubicin previously oxidized with NaIO$_4$, 5 molecules of doxorubicin bound per mole of antibody fragment were obtained.

Antibody immunoreactivity after conjugation was measured by loading 200 μg of (L19-doxo) conjugate onto 200 μl of ED-B-Sepharose resin (capacity>2 mg ED-B/ml resin) on a pasteur pipette, followed by absorbance measuring at 496 nm of the flow-through and eluate fractions. Immunoreactivity, defined as the ratio between the absorbance values of the eluted fraction and the sum of the values of the eluted and the flow-through fractions, was 30%.

Cytotoxicity Test

In a 15 ml Falcon tube, a sample of scFv-doxo conjugate (2 ml) was dialyzed against PBS (4 ml) shaking at 37° C. using a molecular weight cut off (MWCO) membrane of 12,000-14,000 (Socochim S A, Switzerland).

At different time intervals, the dialysis buffer was withdrawn and filtered. The amount of doxorubicin released was measured from the absorbance at 496 nm and the integration of the signal obtained by reverse phase HPLC (FIG. 8). For the evaluation of the activity of the released drug, a colorimetric cytotoxicity assay in microtitration plates was used based on quantification of biomass by staining cells with Crystal Violet (Serva). Unconjugated doxorubicin and doxorubicin released from the conjugate were analyzed in parallel.

C51 murine adenocarcinoma cells were seeded in 24-well plates at a density between $10^6$ and $10^7$ cells per well. The plates were incubated overnight at 37° C. in humidified, 5% $CO_2$ atmosphere to ensure the growth of the monolayer. The medium was then removed and different concentrations of doxorubicin was added. Relative cell numbers in treated and control plates were determined by crystal violet staining. Quantification is possible by solubilising the absorbed dye in ethanol 70% and determining optical density at 590 nm where absorbance is directly proportional to cell number. Relative cell number can be expressed as $T/C = T-C_0/C-C_0 \times 100$ [T=absorbance of treated cultures, C=absorbance of control cultures, and $C_0$=absorbance of cultures at the start of incubation (t=0)]. The results of this study are depicted in FIG. 9.

In Vivo Anti-Tumor Activity

A set of 6 nude mice previously injected subcutaneously with C51 adenocarcinoma cells, received intravenous injections of doxo conjugated to scFv(L19) via periodate oxidation. At the same time points, a set of five mice received injection of saline buffer.

Five injections were administrated to the mice each corresponding to about 18 μg of doxorubicin derivative (less than one tenth of the maximal tolerated dose for intravenously injected doxorubicin, i.e. 8 mg/kg).

The tumors of the mice treated with (L19-doxo) were measured regularly with a caliper and grew slower than the tumors in the untreated mice. Fourteen days after the tumor grafting, the average volume of the tumors in treated animals was about half of the average volume of the tumors in non treated animals. (FIG. 10).

Example 4

Figure 11:
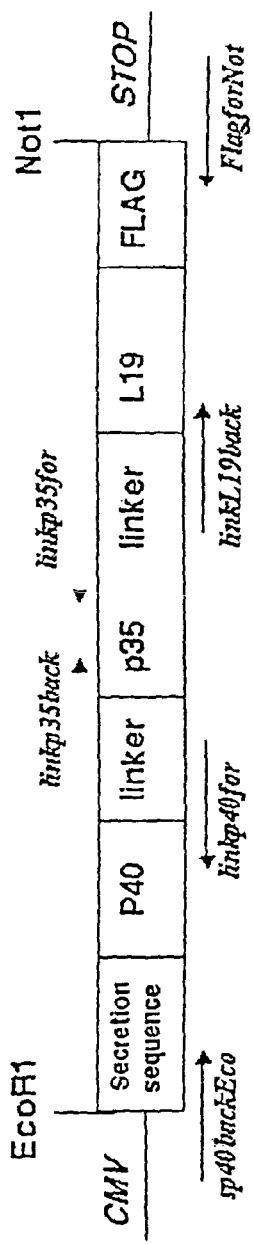
FIG. 11 shows a schematic representation of the IL12-L19 cDNA construct. The p35 and p40 subunits were genetically fused with DNA linker encoding for 15 amino acids (GGGGS)$_3$ (SEQ ID NO: 2) and further fused to the L19 sequence by another linker of 6 amino acids (GSADGG (SEQ ID NO: 3)). The entire fusion protein encoding sequence was cloned into the pcDNA3.1 mammalian expression vector using the EcoR1 and Not1 restriction sites, as described below. sp40backEco, linkp40for, linkp35back, linkp35for, linkL19back, and FlagforNot are primers used in the PCR amplification described in the experimental description below.

Preparation of DNA Construct Encoding an IL12-L19 Fusion Protein and Production of the Fusion Protein Preparation of DNA Construct A schematic representation of the IL12-L19 cDNA construct is given in FIG. 11. The gene fusion was constructed by performing two rounds PCR assembly from the individual genes of the murine IL-12 subunits p35 and p40 and of scFv (L19).

The sequence of the murine IL-12 subunits p35 and p40 were obtained from ATTC (American Type Culture Collection, Manassas, Va. 20110, USA) and amplified by PCR with the following primers:

The primer sp40backEco (5' ccg gaattc atg tgt cct cag aag cta acc atc 3' (SEQ ID NO: 12)) anneals to the endogenous secretion sequence of p40 and appends to its 5' end a restriction site for the endonuclease EcoR1.

The primer linkp40for (5' cc gcc acc gct ccc tcc gcc acc gga acc tcc ccc gcc gga tcg gac cct gca ggg aac 3' (SEQ ID NO: 13)) introduces to the 3' end of p40 a part of the (Gly$_4$Ser)$_3$-linker (SEQ ID NO: 2) to allow its PCR assembly to the 5' end of p35.

The primer linkp35back (5' ggc gga ggg agc ggt ggc gga ggt tcg agg gtc att cca gtc tct gga cct 3' (SEQ ID NO: 14)) introduces to the 5' end the complementing sequence of the (Gly$_4$Ser)$_3$-linker (SEQ ID NO: 2) for PCR assembly with p40.

The primer linkp35for (5' ctc acc tcc atc agc gct tcc ggc gga gct cag ata gcc 3' (SEQ ID NO: 15)) anneals to the 3' end of p40 and appends the sequence of a short amino acid linker (GSADGG (SEQ ID NO: 3)) to connect the p45 subunit of IL12 and L19.

The gene sequence of L19 with a FLAG tag was PCR amplified with the following primers:

The primer linkL19back (5' gcc gga agc gct gat gga ggt gag gtg cag ctg ttg gag tc 3' (SEQ ID NO: 16)) appends to 5' end of L19 the complimentary DNA sequence of the short amino acid linker (GSADGG (SEQ ID NO: 3)) between p35 and L19.

The primer FlagforNot (5' a agg aaa aaa gcggccgc cta ttt gtc atc atc gtc ttt gta gtc 3' (SEQ ID NO: 17)) anneals to the Flag sequence of L19Flag and introduces a stop codon as well as a restriction site for the endonuclease Not1 at the 3' end.

Nucleic acid encoding IL12-L19 was constructed by performing two rounds of PCR assembly. First, the p40 and p35 fragments were fused by PCR assembly, using primers sp40backEco and linkp35for. In a second PCR assembly step with the primers sp40backEco and FlagforNot, the DNA fragment encoding p40-linkers-p35 was fused to the 5' end of L19. The assembled IL12-L19 was cloned into the mammalian cell expression vector pcDNA3.1 (+) vector (Invitrogen, Croningen, The Netherlands), using the EcoR1/Not1 sites of the vector.

Expression and Purification of IL12-L19

HEK 293 cells (Human embryonic kidney cells) were transfected with the vector and stable transfectants selected in the presence of G418 (500 µg/ml). Clones of G418-resistant cells were screened for IL12 expression by ELISA using recombinant ED-B domain of Human fibronectin as antigen.

The IL12-L19 fusion protein was purified from cell culture medium by affinity chromatography over ED-B conjugated to Sepharose. The size of the fusion protein was analysed in reducing conditions on SDS-PAGE and in native conditions by FPLC gel filtration on a Superdex S-200 (Amersham Pharmaceutica Biotech, Uppsala, Sweden).

Determination of IL 12 Bioactivity

Figure 12:
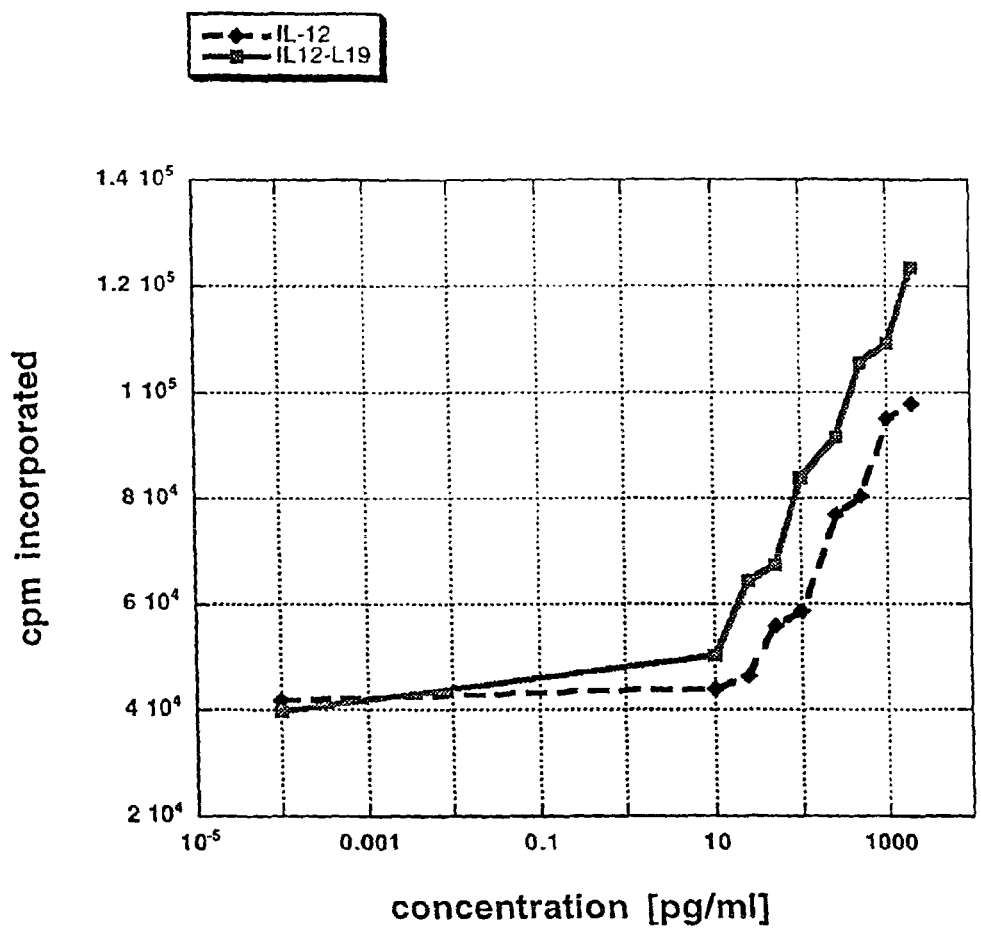
FIG. 12 shows the biological activity of IL12 moiety of the fusion protein in comparison with commercially available recombinant murine IL12 as measured in a T cell proliferation assay.

The IL12 activity of the IL12-L19 fusion protein was determined by performing a T cell proliferation assay (Gately et al., Current Protocols in Immunology, 1997). Resting human peripheral blood monocytes (PBMC) were cultured with mitogen (phytohemagglutinin and IL-2) for 3 days and then incubated with serial dilutions of either fusion protein or commercially available, recombinant, murine IL12 standard. Proliferation was subsequently measured by [$^3$H]thymidine incorporation (FIG. 12).

Example 5

In Vivo Treatment with IL12-L19 Fusion Protein

Figure 13:
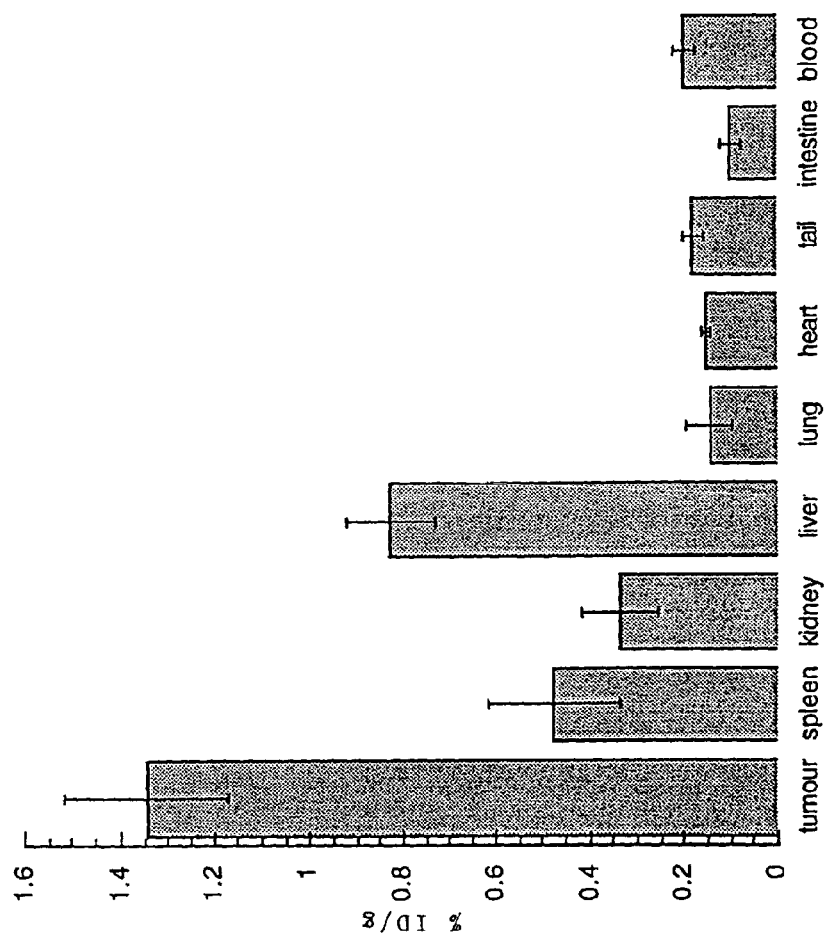
FIG. 13 shows the results of a biodistribution analysis performed in mice bearing subcutaneously implanted F9 teratocarcinoma which were injected intravenously with radioiodinated IL12-L19 fusion protein.

In vivo targeting activity was analysed by performing biodistribution experiments with radioiodinated fusion protein in nude mice (RCC Füllinsdorf) bearing subcutaneously grafted F9 murine teratocarcinoma (Tarli et al., 1999). Biodistribution data were obtained from mice sacrificed at 1, 4 and 24 hours after injection. At these time points, the tumor, the organs and the blood were removed, weighed and radioactivity counted. Targeting results were expressed as a percent injected dose per gram of tissue (% ID/g). The results are shown in FIG. 13.

BALB/c mice (RCC Füllinsdorf) were injected subcutaneously with 5×10$^6$ cells of C51 colon carcinoma. Two therapy experiments, with five or six animals per group each, were performed on either small or large tumor bearing mice.

In the first case, therapy was started four days after tumor cell injection, when small tumors were clearly visible (≈30 mm$^3$). In the treated group, mice were injected into the tail vein with 2.5 µg of IL12-L19 fusion protein every 48 hours. The control group received PBS injections according to the same schedule. At the end of the treatment, animals were sacrificed, tumors were weighed and organs and tumors were placed in fixative for histological analysis.

Figure 14:
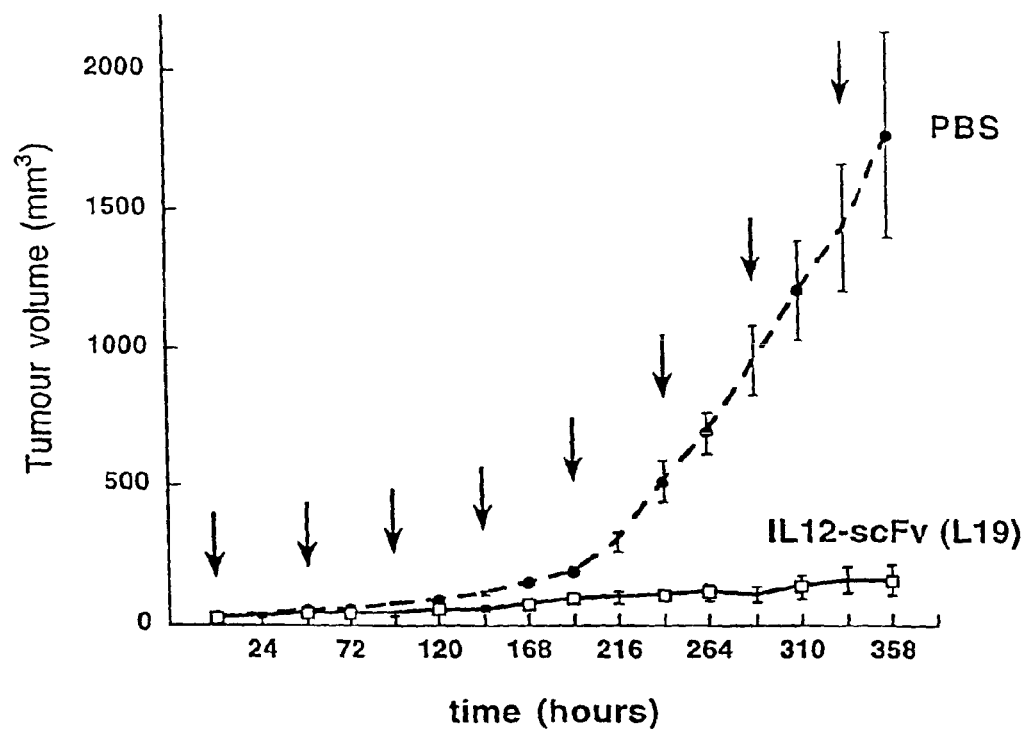
FIG. 14 shows a plot (versus time in hours) of the volume of C51 colon carcinoma tumors (in mm$^3$) subcutaneously implanted in mice which have been injected (indicated by arrows) with either PBS or 2.5 µg of IL12-L19 fusion protein every 48 hours. Injections were started when tumors were small ($\approx$30 mm$^3$).

The results are shown in FIG. 14.

In a second experiment, therapy was started when the average tumor volume had reached 300 mm$^3$. Mice of the treated group were subsequently injected intravenously with 10 µg of IL12-L19 fusion protein every 48 hours, with the control group receiving PBS injections, respectively.

Figure 15:
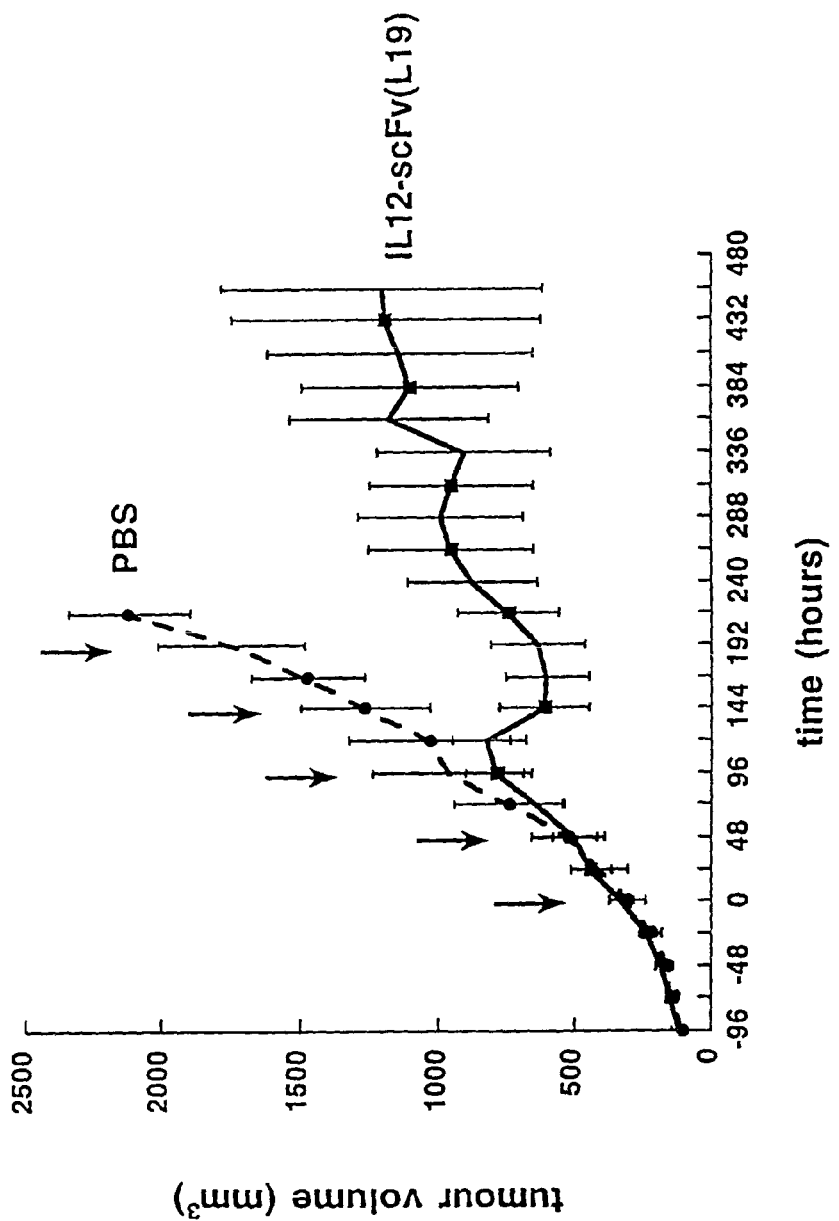
FIG. 15 shows a plot (versus time in hours) of the volume of C51 colon carcinoma tumors (in mm$^3$) subcutaneously implanted in mice which have been injected (indicated by arrows) with either PBS or 10 µg of IL12-L19 fusion protein every 48 hours.
Figure 16:
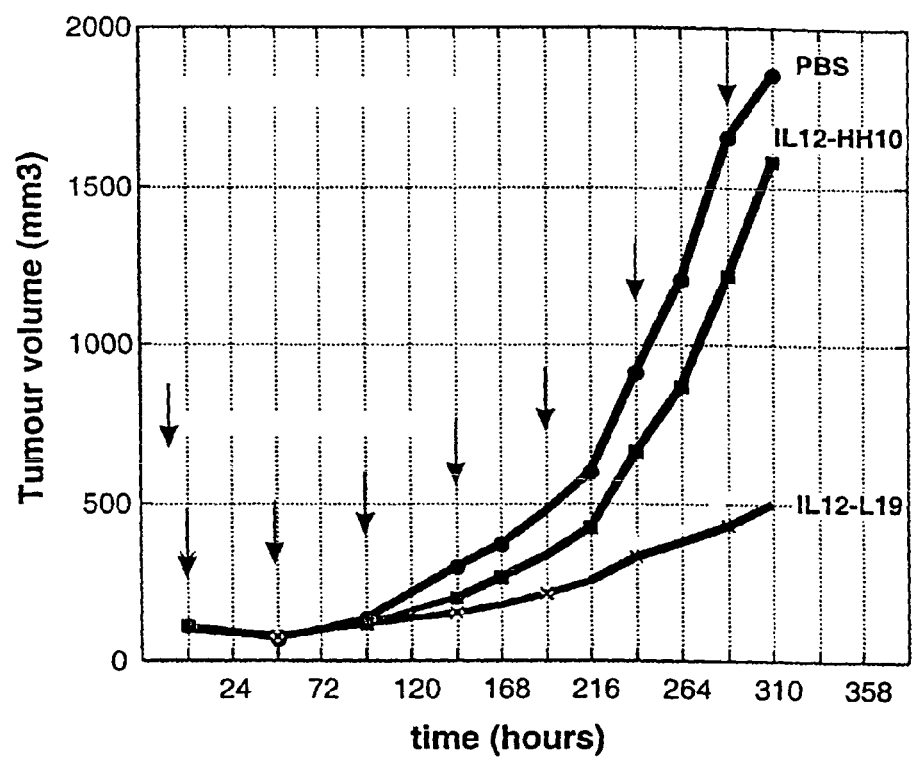
FIG. 16 shows a plot (versus time) of the volume of C51 colon carcinoma tumors subcutaneously implanted in mice which have been injected (indicated by arrows) with PBS, IL12-HyHEL10 fusion protein (2.5 µg/injection) or IL12-L19 fusion protein (2.5 µg/injection) every 48 hours.

The results are shown in FIG. 15.

Example 6

ScFv(L19)-Interferon-γ

The present inventors have found that when targeting the L19-interleukin-12 fusion protein to tumor vasculature in tumor bearing mice, they have observed increased levels of IFN-γ in the blood. In contrast, no elevated levels of IFN-γ could be detected with a non-targeted scFv-interleukin-12 fusion protein.

The inventors have investigated two avenues for fusing IFN-γ to scFv (such as L19). Previously, there has been a difficulty represented by the fact that IFN-γ needs to be homodimeric in order to be biologically active. A fusion protein between IFN-γ and (either the heavy chain or the light chain of) an IgG (which is, in turn, a homodimeric molecule), would result in the non-covalent polymerisation/precipitation of the resulting fusion protein.

Figure 17:
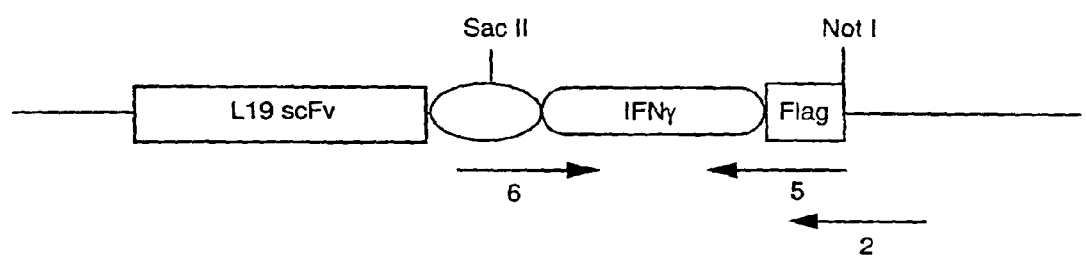
FIG. 17 illustrates a construct encoding a fusion protein wherein a monomer of IFN-γ is fused at the C-terminal extremity of scFv(L19). IFN-γ causes homodimerisation of the fusion protein.

In the first approach (FIG. 17), IFN-γ monomer was fused at the C-terminal extremity of scFv. The resulting fusion protein was well expressed in stably-transfected mammalian cell culture, yielding a pure protein (after affinity chromatography on ED-B resin), with an apparent molecular weight of 43 kDalton in reducing SDS-PAGE. The protein was mainly homodimeric in solution, as determined by gel-filtration chromatography using a Superdex-200 column (Amersham-Pharmacia, Dübendorf, Zürich, Switzerland). Both the scFv and the IFN-γ moieties were shown to be active in the fusion protein, since scFv (actually L19)-IFN-γ was able to bind with high-affinity to the ED-B domain of fibronectin and to block the proliferation of tumor cells, in a typical IFN-γ-dependent fashion.

Figure 18:
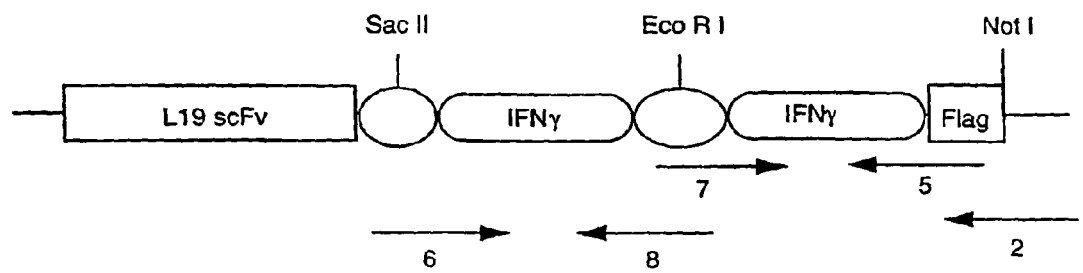
FIG. 18 illustrates a construct encoding a fusion protein wherein a single-chain homodimeric IFN-γ is fused at the C-terminal extremity of scFv(L19). In solution, the protein dimerises non-covalently, giving rise to a protein of MW=125 kDa.

In the second approach (FIG. 18), IFN-γ homodimer (consisting of two IFN-γ joined together by a polypeptide linker) was fused at the C-terminal extremity of scFv(L19). The resulting fusion protein was well expressed in stably-transfected mammalian cell culture, yielding a pure protein (after affinity chromatography on ED-B resin), with an apparent molecular weight of 59 kDalton in reducing SDS-PAGE. The protein was mainly homodimeric in solution, as determined by gel-filtration chromatography using a Superdex-200 column (Amersham-Pharmacia, Dübendorf, Zürich, Switzerland). The nature of the fusion protein in solution, with four antigen-binding sites and four IFN-γ monomeric units, is compatible with biological activity. The fusion protein showed strong binding to the ED-B domain of fibronectin both by ELISA and by BIAcore analysis, and it was able to block the proliferation of tumor cells, in a typical IFN-γ-dependent fashion.

The anti-tumor activities of scFv(L19)-IFN-γ and scFv (L19)-(IFN-γ)$_2$ are demonstrated in tumor-bearing mice.

Experimental Procedures

Primer Sequences are shown in Table 4.

Cloning of L19-IFN-γ into the pcDNA3.1(+) Vector: Plasmid pIS14.

Murine IFN-γ coding sequence (purchased from ATCC, Manassas, Va. 20110, USA, ATCC No. 63170) was amplified using primers 6 and 5. In a second PCR reaction, a peptidic Flag tag was appended at the C-terminus of the fusion protein using primers 6 and 2.

Figure 19:
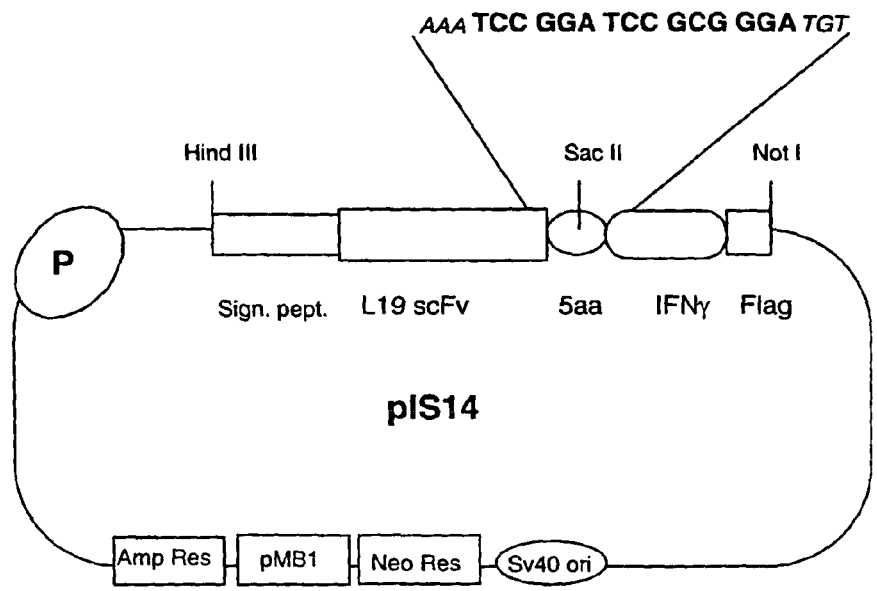
FIG. 19 illustrates vector pIS14 that encodes a fusion protein comprising the L19 scFv and monomeric IFN-γ.

The resulting insert was purified, digested with Sac II/Not I and ligated in a Sac II/Not I double digested modified pcDNA3.1(+) vector. The vector had previously been modified as follows: An IgG secretion sequence was fused N-terminally to the scFv (L19) and the construct was cloned HindIII/Eco RI into the pcDNA3.1(+) vector. C-terminal of the scFv (L19) is a short 5 amino acid linker encoded by TCC GGA TCC GCG GGA (SEQ ID NO: 27). See FIG. 19.

Cloning of L19-(IFN-γ)$_2$ into the pcDNA3.1(+)Vector: Plasmid pIS16.

Figure 20:
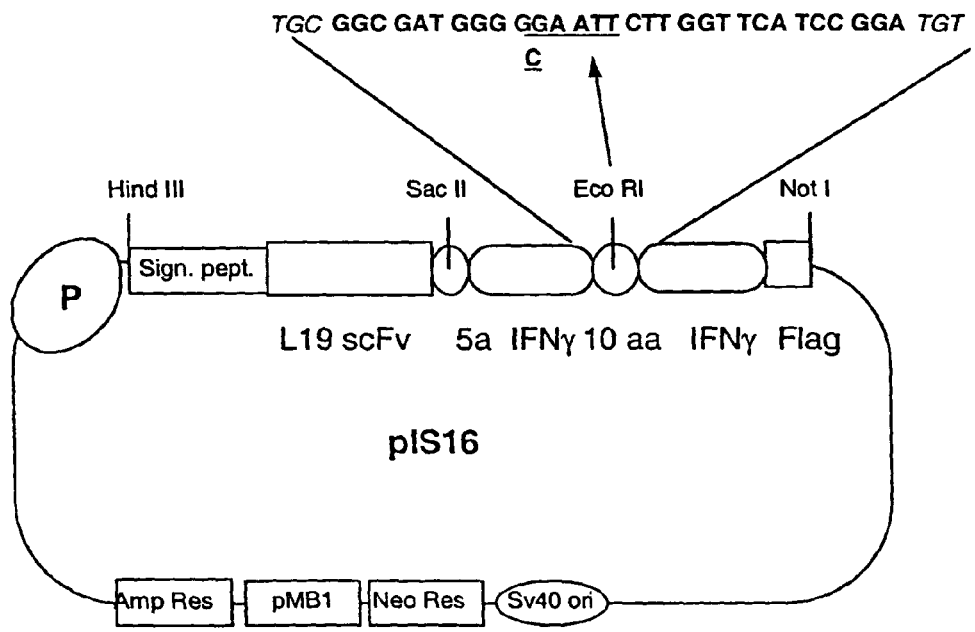
FIG. 20 illustrates vector pIS16 that encodes a fusion protein comprising the L19 scFv and dimeric IFN-γ.

The murine IFN-γ dimer was cloned by ligating two separately amplified IFN-γ monomers. One IFN-γ monomer was amplified using primers 6 and 8, thus appending a Sac II restriction site to the 5' end, and a 10 amino acid linker encoded by GGC GAT GGG GGA ATT CTT GGT TCA TCC GGA (SEQ ID NO: 29) containing an internal EcoR I restriction site to the 3'end. See FIG. 18. The second IFN-γ monomer was amplified with primers 7 and 5, followed by a second PCR reaction, using primers 7 and 2, thus adding the 10 amino acid linker containing an internal EcoR I restriction site to the 5' end, and a peptidic Flag-tag followed by a Not I restriction site to the 3' end. The two fragments corresponding to monomeric subunits of IFN-γ were digested with EcoRI and ligated. The band corresponding to the ligation product was gelpurified on an agarose gel, digested with Sac II/Not I and ligated into the Sac II/Not I double digested modified pcDNA3.1(+) vector. The vector had previously been modified as follows: An IgG secretion sequence was fused N-terminally to the scFv (L19) and the construct was cloned HindIII/Eco RI into the pcDNA3.1(+) vector. C-terminal of the scFv (L19) is a short 5 amino acid linker (see FIG. 20).

Expression and Purification of L19-IFN-γ and L19-(IFN-γ)$_2$

HEK 293 cells (human embryonic kidney cells) were transfected with the vector pIS14 and pIS16 and stable transfectants selected in the presence of G418 (500 µg/ml) using standard protocols (Invitrogen, Groningen, The Netherlands). Clones of G418-resistant cells were screened for IFN-γ expression by ELISA using recombinant ED-B domain of human fibronectin as antigen. The L19-IFN-γ and L19-(IFN-γ)$_2$ fusion proteins were purified from cell culture medium by affinity chromatography over a ED-B conjugated CM Sepharose column. The size of the fusion protein was analyzed in reducing conditions on SDS-PAGE and in native conditions by FPLC gel filtration on a Superdex S-200 column (Amersham Pharmacia Biotech, Uppsala, Sweden).

Example 7

Construction and In Vivo Anti-Tumor Activity of Antibody mTNFα Fusion

Materials and Methods

Construction and Expression of L19-mTNFα Fusion Protein.

Figure 21:
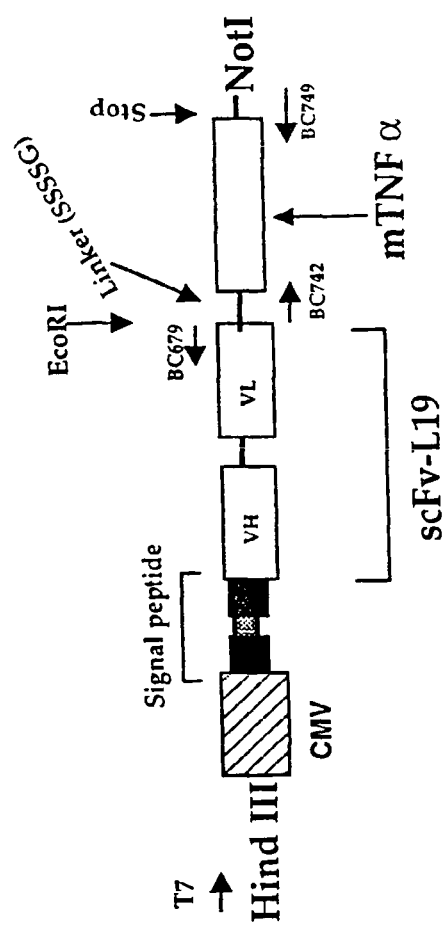
FIG. 21 shows a schematic representation of the scFv L19-mTNFα cDNA construct. scFv L19 and mTNFα cDNA were genetically fused with a DNA linker encoding for 15 amino acids (SSSSG)$_3$ (SEQ ID NO: 1) and cloned into the pcDNA mammalian expression vector using the HindIII and Not I restriction sites. The hatched box represents the CMV promoter sequence, the filled box the genomic sequence of the signal secretion leader peptide (-- intron inside of the genomic sequence) and white boxes the VH or VL of scFV-L19 and mTNFα sequence. T7, BC679, BC742 and BC749 and primers used in the PCR amplifications described in Materials and Methods.
Figure 22:
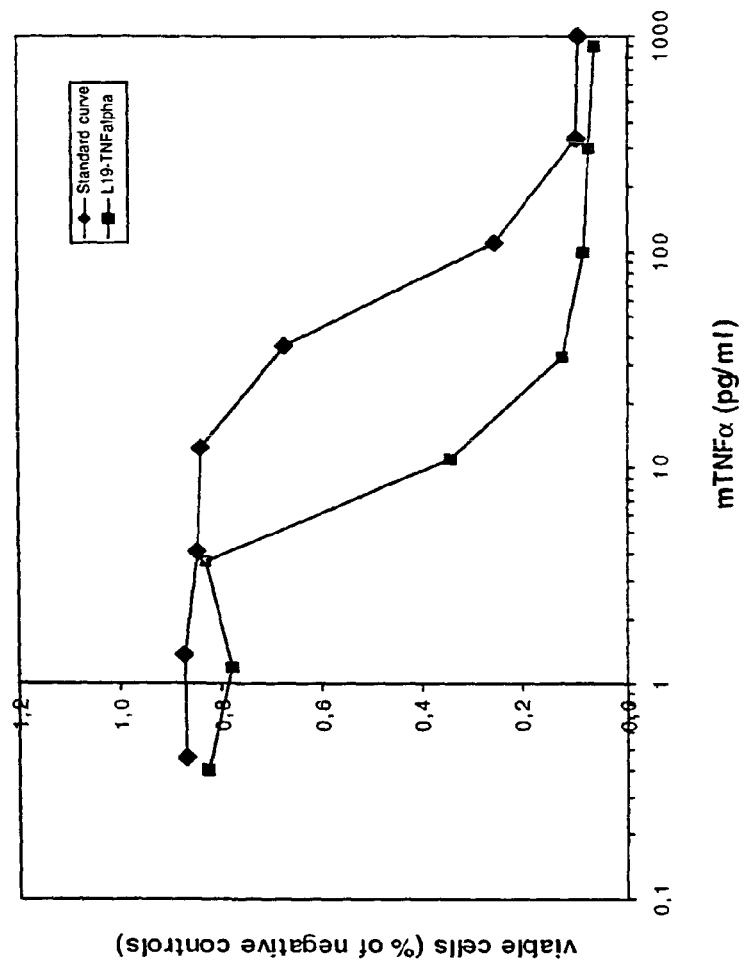
FIG. 22 shows the biological activity of the mTNFα portion of the fusion protein (■) C and of recombinant mTNFα (▲) measured by cytotoxicity assay on mouse L-M fibroblasts (see to Materials and Methods in Example 7).

The L19-mTNFα cDNA was constructed by fusion of a synthetic sequence coding for mouse TNFα (Pennica et al., *Proc. Natl. Acad. Sci USA*, 82: 6060-6064, 1985) to the 3' end of the sequence coding for the scFV L19. The schematic representation of L19-mTNFα cDNA construct is shown in FIG. 21. TNFα cDNA was amplified by Polymerase Chain Reaction (PCR) using BC742 and BC749 primers and, as template the mTNFα cDNA produced by Reverse Transcriptase-Polymerase Chain Reaction (RT-PCR) starting from RNA obtained from the spleen of immunized mice.

The forward primer (BC742) for mouse TNFα (sequence: 5'CTCGAATTCTCTTCCTCATCGGGTAG-TAGCTCTTCCGGCTCATCGTCCAGCGGCC TCAGAT-CATCTTCTCAAAAT3' (SEQ ID NO: 31)) contained the EcoRI restriction enzyme sequence, a 45 bp encoding for a 15 amino acids linker (Ser$_4$Gly)$_3$ (SEQ ID NO: 1) and 21 bases of the mature mouse TNFα sequence (Pennica et al., 1985).

The reverse BC-749 primer (sequence 5'CTCGCGGC-CGCTCATCACAGAGCAATGACTCCAAAGTA3' (SEQ ID NO: 32)) contained 21 bases of the mature mouse TNFα (Pennica et al., 1985, two stop codons and the Not I restriction enzyme sequence.

The scFv L19, which contained in its 5' end the genomic sequence of the signal secretion peptide as reported by Li et al (*Protein Engineering*, 10:731, 1996 or 1997), was amplified by PCR using T7 primer on the vector pcDNA3.1 (Invitrogen, Croningen, The Netherlands) and the BC 679 primer (sequence: CTCGAATTCtttgatttccaccttggtccc (SEQ ID NO: 6)) containing 21 bp of the 3' end of L19 and the EcoRI restriction enzyme sequence.

The fused gene was sequenced, introduced into the vector pcDNA3.1 containing the Cytomegalovirus (CMV) promoter and expressed in p3U1 cells in the presence of G418 (750 µg/ml, Calbiochem, San Diego, Calif.). Clones of G418-resistant cells were screened for the secretion of L19-mTNFα fusion protein by ELISA using recombinant ED-B domain of human Fibronectin (FN) as antigen for L19 and rabbit anti-murine TNFα polyclonal antibody (PeproTech, UK) as specific reagent for immunoreactive mTNFα.

FN Recombinant Fragments, ELISA Immunoassay and Purification of Fusion Protein L19-mTNFα

Recombinant ED-B FN fragment was produced as described by Carnemolla et al (*Int. J. Cancer,* 68:397, 1996). ELISA immunoassay was performed as reported by Carnemolla at al (1996). The L19-m TNFα fusion protein was purified from the conditioned medium of one positive clone using the recombinant human fibronectin fragment ED-B conjugated to Sepharose, by affinity chromatography, as reported by Carnemolla et al (1996). The size of the fusion protein was analysed in reducing conditions on SDS-PAGE and in native conditions by FPLC on a Superdex S-200 chromatography column (Amersham Pharmacia Biotech, Uppsala, Sweden).

L-M Cytotoxicity Assay

The mTNFα biologic activity of the L19-mTNFα fusion protein was determined by the cytotoxicity assay using mouse L-M fibroblasts as described by Corti et al (*J. Immunol. Methods,* 177: 191-194, 1994). Serial dilutions of L19-mTNFα fusion protein and of recombinant mTNFα ($2 \times 10^7$ units/mg) at concentrations from 1000 to 0.4 pg/ml were used in the cytotoxic assay. Results are expressed as a percent of viable cells with respect to negative controls.

Animal and Cell Lines

Male and female 129 and Balb-C mice (8 week-old) were obtained from Harlan Italy (Correzzana, Milano, Italy). F9, a mouse embryonal carcinoma, mouse L-M fibroblasts and p3U1 mouse myeloma cells were purchased from ATCC (American Type Culture Collection, Rockville, Md., USA); C51, a mouse colon adenocarcinoma cell line derived from Balb/C, was used (Colombo et al., *Cancer Metastasis Rev.,* 16:421-432, 1997).

Biodistribution of L19-mTNFα Fusion Protein

Purified L19-mTNFα was radiolabeled with iodine-125 using the Iodogen method (Salacinski et al., *Anal. Biochem.,* 117: 136, 1981)(Pierce, Rockford, Ill.). After labelling, the immunoreactivity was more than 90%. 129 mice with subcutaneously implanted F9 murine teratocarcinoma were intravenously injected with 4 µg (2 µCi) of protein in 100 µl saline solution. Three animals were used for each time point. Mice were sacrificed at 3, 6, 24 and 48 hours after injection. The organs were weighed and the radioactivity was counted. All organs and tumors were placed in fixative for histological analysis and microautoradiography. Targeting results of representative organs are expressed as percent of the injected dose per gram of tissue (% ID/g).

In Vivo Treatment with L19 mTNFα Fusion Protein

Treatment with purified L19-mTNFα fusion protein was preformed in groups of 3 Balb.C mice each injected subcutaneously with $10^6$ of C51 cells. At day 12 after C51 cell injection, 0.8 µg/g of L19-TNFα fusion protein was injected into the tail vein of each animal. A similar group of 3 animals was injected with Phosphate Saline Buffer, pH 7.4 (PBS). The animals were followed for systemic toxicity (weight loss) and tumor growth daily for 6 days. At the end, animals were sacrificed and tumors were placed in fixative for histological analysis and snap frozen for immunohistochemical analysis.

Microautoradiography Analysis and Immunohistochemistry

Tumor and organ specimens were processed for microautoradiography to assess the pattern of $^{125}$I-L19TNFα fusion protein distribution within the tumors or organs as described by Tarli et al (*Blood,* 94: 192-198, 1999). Immunohistochemical procedures were carried out as reported by Castellani et al (*Int. J. Cancer,* 59: 612-618, 1994).

Results

L19-mTNFα construct and selection of clones expressing L19-mTNFα fusion protein G418 resistant clones were screened for the antibody specificity of the supernatants for the ED-B sequence and for immunoreactive mTNFα by ELISA, as described in Materials and Methods.

Supernatants of clones showing immunological specificity for the ED-B sequence and immunoreactive mTNFα were tested for the TNFα biological activity in the L-M cytotoxicity assay (see Materials and Methods).

L19-mTNFα Fusion Protein was Purified in a Two Step Procedure:
  a) by immunoaffinity chromatography, on ED-B sepharose column followed by
  b) size exclusion chromatography (Superdex 200, Pharmacia)

In SDS-PAGE, the fusion protein showed an apparent molecular mass of about 42 kDa, as expected. Both the immunological activity of the scFv L19 component and the biological activity of the mTNFα component in the purified protein were tested.

Biodistribution of Radiolabeled L19-mTNFα Fusion Protein in Tumor-Bearing Mice

To investigate whether the L19-mTNFα fusion protein was able to efficiently localise in tumoral vessels, as reported for scFv L19 by Tarli et al (*Blood,* 94: 192-198, 1999), biodistribution experiments were performed in F9 teratocarcinoma-bearing mice.

L19-mTNFα fusion protein was shown immunohistochemically to strongly stain blood vessels of glioblastoma tumor. Radioiodinated L19-mTNFα fusion protein was injected in the tail vein of mice with subcutaneously implanted F9 tumors, and L19-TNFα fusion protein distribution was obtained at different time points: 3, 6, 24 and 48 hours. As reported in Table I, 22% of the injected dose per gram of tissue (% ID/g) localised in the tumor 3 hours after injection and after 48 hours more than 9% ID/g was still in the tumor. The localisation of L19-mTNFα fusion protein in the tumoral neovasculature was confirmed by microradiographic analysis. Accumulation of the radiolabeled fusion protein was shown in the blood vessels of the F9 mouse tumor. No accumulation of radiolabeled fusion protein was detected in the vessels of the other organs of tumor bearing mice.

Treatment of Tumor Bearing Mice with L19-mTNFα Fusion Protein

Figure 23:
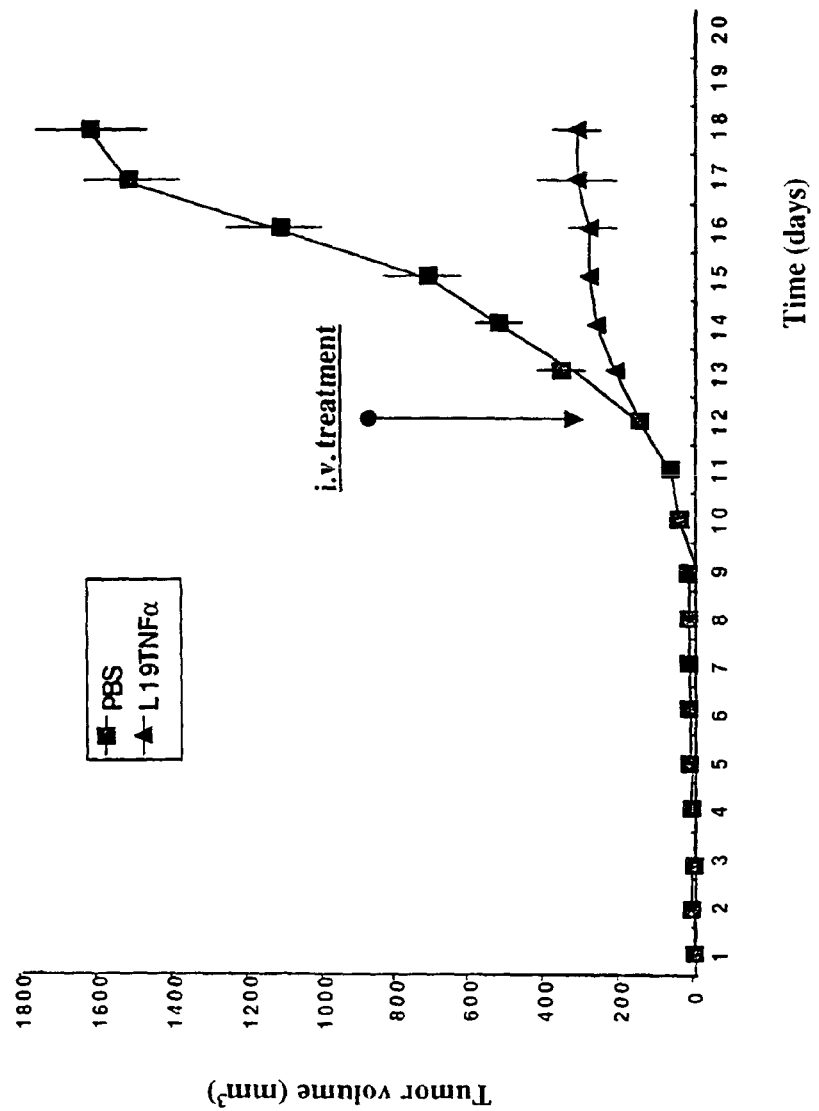
FIG. 23 is a plot (versus time) of the volume of C51 murine colon carcinoma subcutaneously implanted in Balb/C mice which were intravenously injected with either scFV(L19)-mTNF.alpha. or PBS (as negative control). The injection is indicated by the arrow and performed when tumors were approximately 100-200 mm sup.3. Standard errors are indicated.

The efficacy of the L19-mTNFα fusion protein in suppressing tumor growth was tested on one experimental tumor model of mouse adenocarcinoma, C51. For tumor induction, $10^6$ C51 cells were injected subcutaneously in Balb/C animals. After 12 days (when the tumor reaches approximately 100-200 mm$^3$) animals received intravenous injections of either PBS (3 animals) or L19-mTNFα fusion protein (3 animals). The animals were monitored for weight and tumor growth daily for 6 days. The results, summarised in FIG. 23, show a decrease in tumor growth in the group of animals treated with L19-mTNFα fusion protein with respect to animals injected with PBS (bars represent SE). The weight loss was always less than 6% throughout the experiment time.

REFERENCES

1) Folkman Nat. Med. 1: 27, 1995.
2) O'Reilly et al. Nat. Med. 2: 689, 1996.
3) O'Reilly et al. Cell, 88, 277, 1997.
4) Friedlander et al. Science, 270: 1500, 1995.
5) Pasqualini et al. Nat. Biotechnol. 15: 542, 1997.
6) Huang et al. Science, 275: 547, 1997.

7) Kim et al. Nature, 362: 841, 1993.
8) Schmidt-Erfurth et al. Br. J. Cancer, 75: 54, 1997.
9) Zardi et al. EMBO J., 6, 2337-2342 (1987).
10) Carnemolla et al. J. Cell Biol., 108, 1139-1148 (1989).
11) Castellani et al. *Int. J. Cancer,* 59, 612-618 (1994).
12) Tarli et al. Blood, 94: 192-198, 1999.
13) Viti et al. Cancer Res. 59: 347, 1999.
14) Taniguchi et al. Cell 73:5-8, 1993.
15) Rosenberg J. Clin. Oncol. 10:180-199, 1992.
16) Siegel and Puri Interleukin-2 toxicity. J. Clin. Oncol. 9:694-704, 1991.
17) Lode et al. Pharmacol. Ther. 80:277-292, 1998.
18) Meazza et al. Br. J. Cancer, 74: 788-795, 1996.
19) Li et al. Protein Engineering, 10: 731, 1997.
20) Carnemolla et al. Int. J. Cancer 68:397, 1996.
21) Colombo et al. Cancer Metastasis Rev. 16:421-432, 1997.
22) Salacinski et al. Anal. Biochem. 117:136, 1981.
23) Neri et al. Nat. Biotechnol. 15:1271, 1997.

TABLE 1

Biodistribution of Radiolabeled L19-IL2 fusion protein in Tumor-Bearing Mice

| Time (h) | % ID/g | | | | | |
|---|---|---|---|---|---|---|
| | Tumour | Blood | Skin | Liver | Spleen | Kidney |
| 3 | 14.01 ± 2.12 | 6.97 ± 1.14 | 2.73 ± 0.59 | 2.61 ± 0.41 | 3.90 ± 0.97 | 4.69 ± 0.53 |
| 6 | 8.96 ± 1.41 | 2.65 ± 0.73 | 1.48 ± 0.57 | 1.23 ± 0.19 | 2.05 ± 0.41 | 1.98 ± 0.34 |
| 24 | 4.06 ± 1.06 | 0.14 ± 0.04 | 0.58 ± 0.43 | 0.13 ± 0.05 | 0.16 ± 0.05 | 0.19 ± 0.08 |

| Time (h) | % ID/g | | | | |
|---|---|---|---|---|---|
| | Bladder | Thyroid | Heart | Lung | Muscle |
| 3 | 2.16 ± 1.42 | 5.13 ± 0.60 | 2.27 ± 0.45 | 10.32 ± 1.83 | 1.34 ± 0.75 |
| 6 | 6.28 ± 3.98 | 4.98 ± 2.99 | 1.22 ± 0.34 | 5.40 ± 0.61 | 0.53 ± 0.24 |
| 24 | 0.83 ± 0.51 | 0.22 ± 0.12 | 0.09 ± 0.04 | 0.48 ± 0.27 | 0.05 ± 0.02 |

Biodistribution studies were performed as discribed in Materials and Mrthods.
Abbreviation: % ID/g. percent of L19-IL2 fusion protein injected dose per gram of tissue.

TABLE 2

Effect on tumor growth of L19-IL2 fusion protein

| Tumor cells | L19-IL2 fusion protein * | L19 + IL2 | PBS |
|---|---|---|---|
| C51 | 0.017 ± 0.02 [1] | 0.228 ± 0.14 | 0.410 ± 0.17 |
| N592 | 0.173 ± 0.17 | 0.705 ± 0.32 | 1.178 ± 0.75 |
| F9 | 0.061 ± 0.10 [2] | 0.665 ± 0.40 | 1.715 ± 0.57 |

Values reported represent the mean tumor weight (g) ± stdev, groups of six mice for each experiment were used.
[1] A tumoral mass grew only in 4 mice out 6.
[2] A tumoral mass grew only in 3 mice out 6.
* Differences in tumor weights between fusion protein (L19-IL2) treatment and PBS or mixture (L19 + IL2) control groups were statistically significant ($P < 0.01$)

TABLE 3

Statistical comparison (P values) between the different treatment groups in three tumor types.

| | Tumor types | | |
|---|---|---|---|
| Groups compared | F9 | N592 | C51 |
| L19-IL2 fusion protein/PBS | 0.002 | 0.004 | 0.002 |
| L19-IL2 fusion protein/ Mixture (L19 + IL2) | 0.004 | 0.009 | 0.002 |
| Mixture (L19 + IL2)/PBS | 0.004 | 0.093 | 0.093 |

TABLE 4

PRIMER SEQUENCES 2) flagfoNotPicz2
5'-ACT CAG TAA GGC GGC CGC CTA TTA CTT ATC GTC ATC GTC CTT GTA GTC-3' (SEQ ID NO: 18)

3) XbaILI9fo
5'-TCC GTC TAG ATC AGC GCT GCC TTT GAT TTC CAC CTT GGT CCC TTG-3' (SEQ ID NO: 19)

4) IfnXbaba
5'-GGC AGC GCT GAT CTA GAC GGA TGT TAC TGC CAC GGC ACA GTC ATT GAA AGC-3' (SEQ ID NO: 20)

5) Ifnflagfol
5'-ATC GTC ATC GTC CTT GTA GTC GCA GCG ACT CCT TTT CCG CTT-3' (SEQ ID NO: 21)

TABLE 4-continued

PRIMER SEQUENCES

6) IFNBamba
5' AAA TCC GGA TCC GCG GGA TGT TAC TGC CAC GGC ACA GTC (SEQ ID NO: 22)

7) IFNEcoba
5' GAT GGG GGA ATT CTT GGT TCA TCC GGA TGT TAC TGC CAC GGC ACA GTC ATT GAA 3' (SEQ ID NO: 23)

8) IFNEcofo
5' GGA TGA ACC AAG AAT TCC CCC ATC GCC GCA GCG ACT CCT TTT CCG CTT 3' (SEQ ID NO: 24)

9) SegPicback
5' G CCA TTT TCC AAC AGC ACA AAT AAC GGG TT 3' (SEQ ID NO: 25)

10) SeqPicfor
5' G ATG ATG GTC GAC GGC GCT ATT GAG 3' (SEQ ID NO: 26)

TABLE 5

Biodistribution of radiolabeled L19-TNFa fusion protein in tumor-bearing mice

| Time(h) | Tumor | Blood | Skin | Liver | Spleen | Kidney | Bladder | Thyroid | Heart | Lung | Muscle |
|---|---|---|---|---|---|---|---|---|---|---|---|
| | | | | | | % ID/g | | | | | |
| 3 | 22.02 ± 2.3 | 8.39 ± 5.0 | 2.83 ± 1.3 | 8.42 ± 1.9 | 9.08 ± 2.0 | 7.96 ± 3.0 | 37.52 ± 26.7 | 3.21 ± 0.8 | 2.69 ± 0.7 | 6.56 ± 1.7 | 1.33 ± 0.3 |
| 6 | 11.57 ± 2.7 | 2.13 ± 0.9 | 1.68 ± 0.9 | 2.39 ± 0.9 | 3.29 ± 0.9 | 6.06 ± 5.2 | 18.14 ± 9.1 | 2.91 ± 1.8 | 1.32 ± 0.5 | 2.79 ± 1.4 | 0.76 ± 0.2 |
| 24 | 9.77 ± 1.4 | 0.09 ± 0.0 | 0.03 ± 0.0 | 0.15 ± 0.0 | 0.13 ± 0.0 | 0.18 ± 0.0 | 2.9 ± 2.2 | 1.93 ± 0.5 | 0.06 ± 0.0 | 0.18 ± 0.1 | 0.05 ± 0.0 |
| 48 | 9.55 ± 1.7 | 0.01 ± 0.0 | 0.01 ± 0.0 | 0.02 ± 0.0 | 0.01 ± 0.0 | 0.05 ± 0.0 | 0.08 ± 0.0 | 0.0 ± 0.0 | 0.01 ± 0.0 | 0.02 ± 0.0 | 0.0 ± 0.0 |

Biodistribution studies were performed as described in Materials and Methods

Abbreviation: % ID/g, percent of L19-TNFa fusion protein injected dose per gram of tissue

The invention claimed is:

1. A conjugate of
   (i) an antibody, or an antigen binding fragment thereof, which is specific for fibronectin ED-B comprising the VH domain and/or the VL domain of antibody L19
   and
   (ii) TNF-α.

2. A conjugate according to claim 1 wherein said antibody is the L19 antibody.

3. A conjugate according to claim 1 wherein the antibody or an antigen binding fragment thereof is a single-chain.

4. A conjugate of
   (i) an antibody or an antigen binding fragment thereof which is specific for fibronectin ED-B comprising the VH domain and/or the VL domain of antibody L19 which has respectively the VH and/or VL amino acid sequence encoded by the DNA insert of ATCC deposit no. PTA-9529
   and
   (ii) TNF-α.

5. A conjugate of
   (i) an antibody or an antigen binding fragment thereof which is specific for fibronectin ED-B comprising the domain having the sequence EVQLLESGGGLVQPGGSLRLSCAASGFTFSSFSMSWVRQAPGKGLEWVSSISGSSGTTYYADSVKGRFTISRDNSKNTLYLQMNSLRAEDTAVYYCAKPFPYFDYWGQGTLVTVSS (SEQ ID NO: 34) and/or the domain having the sequence EIVLTQSPGTLSLSPGERATLSCRASQSVSSSFLAWYQQKPGQAPRLLIYYASSRATGIPDRFSGSGSGTDFTLTISRLEPEDFAVYYCQQTGRIPPTFGQGTKVEIK (SEQ ID NO: 35);
   and
   (ii) TNF-α.

6. A pharmaceutical composition comprising a conjugate of claim 1 and a pharmaceutically acceptable carrier.

7. A pharmaceutical composition comprising a conjugate of claim 2 and a pharmaceutically acceptable carrier.

8. A pharmaceutical composition comprising a conjugate of claim 4 and a pharmaceutically acceptable carrier.

9. A pharmaceutical composition comprising a conjugate of claim 5 and a pharmaceutically acceptable carrier.

10. A method of treating angiogenesis in pathological lesions in a patient in need of said treatment, comprising administering a conjugate according to claim 1.

11. A method according to claim 10, wherein the pathological lesion is a tumor.

12. A method of treating angiogenesis in pathological lesions in a patient in need of said treatment, comprising administering a conjugate according to claim 2.

13. A method according to claim 12 wherein said pathological lesion is a tumor.

14. A method of treating angiogenesis in pathological lesions in a patient in need of said treatment, comprising administering a conjugate according to claim 4.

15. A method according to claim 14 wherein said pathological lesion is a tumor.

16. A method for suppressing tumor growth in a patient in need of said treatment, comprising administering a conjugate according to claim 1.

17. A method according to claim 16 wherein said antibody or antigen-binding fragment thereof is L19 antibody.

18. A method of claim 10 further comprising administering another treatment for said pathological lesion.

19. A method according to claim 18, wherein the pathological lesion is a tumor.

20. A method according to claim 19 wherein said antibody or antigen-binding fragment thereof is L19 antibody.

21. A method of claim 14 further comprising administering another treatment for said pathological lesion.

22. A method of claim 16 further comprising administering another treatment for said pathological lesion.

23. A method of treating angiogenesis in pathological lesions in a patient in need of said treatment, comprising administering a conjugate according to claim 5.

24. A method of claim 23 further comprising administering another treatment for said pathological lesion.

\* \* \* \* \*